US011634783B2

(12) United States Patent
Palmisano et al.

(10) Patent No.: US 11,634,783 B2
(45) Date of Patent: Apr. 25, 2023

(54) METHODS FOR DETECTING FUNGI IN TURF GRASS WITH A LAMP ASSAY HAVING NOVEL PRIMER SETS

(71) Applicant: SYNGENTA PARTICIPATIONS AG, Basel (CH)

(72) Inventors: Marilena Palmisano, Wädenswil (CH); Christian Wohler, Wädenswil (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 121 days.

(21) Appl. No.: 16/967,319

(22) PCT Filed: Feb. 5, 2019

(86) PCT No.: PCT/EP2019/052803
§ 371 (c)(1),
(2) Date: Aug. 4, 2020

(87) PCT Pub. No.: WO2019/149963
PCT Pub. Date: Aug. 8, 2019

(65) Prior Publication Data
US 2020/0362424 A1 Nov. 19, 2020

(30) Foreign Application Priority Data

Feb. 5, 2018 (EP) ...................... 18155093
Mar. 2, 2018 (EP) ...................... 18159821

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/16* (2013.01)

(58) Field of Classification Search
CPC .......................... C12Q 1/6895; C12Q 2600/16
See application file for complete search history.

(56) References Cited

U.S. PATENT DOCUMENTS

2013/0116344 A1   5/2013   Di Maiuta et al.

FOREIGN PATENT DOCUMENTS

| CN | 106222263 A | * | 12/2016 | ........... C12Q 1/6844 |
| CN | 104946760 B | * | 12/2017 | ........... C12Q 1/6851 |
| CN | 108060257 A | * | 5/2018 | ........... C12Q 1/6844 |
| WO | 2009147017 A1 | | 12/2009 | |
| WO | 2015067635 A2 | | 5/2015 | |

OTHER PUBLICATIONS

Asano et al., 2010. Development of multiplex PCR to detect five *Pythium* species related to turfgrass diseases. Journal of phytopathology, 158(9), pp. 609-615. (Year: 2010).*
Fukuta et al., 2013. Detection of Pythium aphanidermatum in tomato using loop-mediated isothermal amplification (LAMP) with species-specific primers. European journal of plant pathology, 136(4), pp. 689-701. (Year: 2013).*
Genbank Accession No. AB513047—*Pythium ultimum* var. *ultimum* gene for28S rRNA, partial sequence, strain: NBRC 100122, submitted Jul. 2012, retrieved on Mar. 30, 2022 from http://www.ncbi.nlm.nih.gov/nuccore/AB513047). (Year: 2012).*
Nagamine et al., 2002. Accelerated reaction by loop-mediated isothermal amplification using loop primers. Molecular and cellular probes, 16(3), pp. 223-229. (Year: 2002).*
Notomi et al., 2000. Loop-mediated isothermal amplification of DNA. Nucleic acids research, 28(12), e63—pp. 1-7. (Year: 2000).*
Shen et al., 2017. Development of a loop-mediated isothermal amplification method for the rapid detection of Pythium ultimum. Australasian Plant Pathology, 46(6), pp. 571-576. (Year: 2017).*
Denschlag et al., 2014. Real-time loop-mediated isothermal amplification (LAMP) assay for group specific detection of important trichothecene producing *Fusarium* species in wheat. International journal of food microbiology, 177, pp. 117-127. (Year: 2014).*
Fukuta et al., Epub Dec. 15, 2016. Detection of Fomitiporia torreyae and Fulviformes umbrinellus by multiplex loop-mediated isothermal amplification (mLAMP) for diagnosis of Japanese pear dwarf. Annals of Applied Biology, 2017, 170(2), pp. 170-178. (Year: 2016).*
Tanner, N.A., Zhang, Y. and Evans Jr, T.C., 2012. Simultaneous multiple target detection in real-time loop-mediated isothermal amplification. Biotechniques, 53(2), pp. 81-89. (Year: 2012).*
Genbank Accession No. DQ448301—Sclerotinia homoeocarpa elongation factor-1 alpha gene, partial sequence, submitted by Mar. 15, 2006, retrieved on Jun. 14, 2022 from (Year: 2006).*
Cao et al., 2016. Rapid and quantitative detection of Pythium inflatum by real-time fluorescence loop-mediated isothermal amplification assay. European Journal of Plant Pathology, 144(1), pp. 83-95. (Year: 2016).*
English translation of CN106222263A, published Dec. 14, 2016. (Year: 2016).*
English translation of CN104946760B, published Dec. 8, 2017. (Year: 2017).*

(Continued)

*Primary Examiner* — Gary Benzion
*Assistant Examiner* — Olayinka A Oyeyemi
(74) *Attorney, Agent, or Firm* — BakerHostetler; Toni-Junell Herbert

(57) ABSTRACT

The present invention provides a method for detecting fungal DNA in a turf grass sample with a loop-mediated isothermal amplification (LAMP) assay which contains primers for fungal DNA of at least one turf pathogenic fungi selected from *Sclerotinia homoeocarpa, Rhizoctonia solani* spp., *Pythium ashanidematum, Gaeumannomyces graminis* spp., *Microdochium nivale* spp., *Magnaporthe poae, Colletotrihum graminicola, Colletotrichum cereale* and *Pytium ultimum* var. *ultimum*, comprising: subjecting the turf sample to a LAMP reaction wherein the LAMP reaction uses a primer set of four or more nucleic acid sequences with each primer in the set having from 15 to 50 nucleic acids The primers useful in the present method are selected from specifically selected internal transcribed spacer regions or genes of the target fungi to provide improved assay results.

7 Claims, No Drawings
Specification includes a Sequence Listing.

(56) References Cited

OTHER PUBLICATIONS

English translation of CN108060257A, published May 22, 2018. (Year: 2018).*
Partial International Search Report of International Application No. PCT/EP2019/052803 dated Mar. 29, 2019.
International Search Report and Written Opinion for International Application No. PCT/EP2019/052803 dated Jul. 3, 2019.
Patel et al.: Implementation of Loop-Mediated Isothermal Amplification Methods in Lateral Flow Devices for the Detection of Rhizoctonia Solani; Canadian Journal of Plant Pathology, vol. 37 (1); pp. 118-119; 2015.
Shen Danyu et al.: Development of a Loop-Mediated Isothermal Amplification Method for the Rapid Detection of Pythium Ultimum; Australasian Plant Pathology, Adelaide, AU, vol. 46 (6), pp. 571-576; 2017.
Chenchen Lu et al.: Rapid Diagnosis of Soybean Seedling Blight Caused by Rhizoctonia Solani and Soybean Charcoal Rot Caused by Macrophomina Phaseolina Using Lamp Assays Phytopathology, vol. 105 (12), pp. 1612-1617; 2015.
Fukuta Shiro et al.: Detection of *Pythium aphanidermatumin* Tomato Using Loop-Mediated Isothermal Amplification (LAMP) With Species-Specific Primers; European Journal of Plant Pathology, Springer Netherlands, NL, vol. 136 (4), pp. 689-701; 2013.
Ahmed et al.: Discriminatory Simplex and Multiplex PCR for Four Species of The Genus*Sclerotinia*; Journal of Microbiological Methods, Elsevier, Amsterdam, NL vol. 92 (3), pp. 293-300; 2012.
Abd-Elmagid Ahmed et al.: Discriminatory Simplex and Multiplex PCR for Four Species of The Genus*Sclerotinia*; Journal of Microbiological Methods, Elsevier, Amsterdam, NL, vol. 92 (3), pp. 293-300; 2012.
Devries et al.: Genetic Analysis of Fungicide-Resistant Sclerotinia Homoeocarpa Isolates From Tennessee and Northern Mississippi; Plant Disease, vol. 92 (1), pp. 83-90; 2008.

\* cited by examiner

METHODS FOR DETECTING FUNGI IN TURF GRASS WITH A LAMP ASSAY HAVING NOVEL PRIMER SETS

CROSS-REFERENCE TO RELATED APPLICATIONS

This application is a 371 National Stage application of International Application No. PCT/EP2019/052803 filed Feb. 5, 2019 which claims priority to EP 18155093.0, filed Feb. 5, 2018, and EP 18159821.0, filed Mar. 2, 2018, the entire contents of which applications are hereby incorporated by reference.

The present invention relates to a method of detecting diseases in turf grass caused by fungal pathogens with a loop-mediated isothermal amplification (LAMP) assay of a sample of such turf grass to detect nucleic acids from one or more fungi.

LAMP or Loop-mediated Isothermal Amplification as described in e.g. U.S. Pat. No. 6,410,278 (Eiken) is a DNA amplification method characterized by the use of at least 4 or more different primers that are specifically designed to recognize 6 distinct regions on the target gene and the reaction process proceeds at a constant temperature using strand displacement reaction. Amplification and detection of target nucleic acid of interest can be completed in a single step, by incubating the mixture of the biological sample or a nucleic acid extract thereof, primers, DNA polymerase with strand displacement activity and substrates at a constant temperature (about 65'C). It provides high amplification efficiency, with DNA being amplified numerous times in 15-60 minutes. Because of its high specificity, the presence of amplified product can indicate the presence of target gene.

There are numerous problems that turf grass managers face in maintaining turf grass at a standard of quality expected by users. While the problems are many, those relating to disease (including diseases caused by fungal pathogens) are particularly challenging to manage and control. For example, disease can affect turf grass plants on golf courses causing a loss of revenue from reduced quality including playability. One example of a common problem for golf course managers is knowing which disease is present so that appropriate and timely management techniques can be taken. Relevant turf diseases caused by turf pathogenic microorganisms include, for example, anthracnose, take-all patch, summer patch, snow mold, *Pythium* blight, brown patch and dollar spot.

Agricultural active chemicals for controlling pathogens, such as fungicides, are typically applied on golf courses as needed depending on the extent of disease pressure, pathogen population, weather, and the like. However, fungicide applications are highly controlled by course budget, availability of appropriate equipment, and availability of qualified personnel for applying the agricultural active chemicals.

In view of these problems, a rapid and reliable assay for detection of turf pathogenic fungi would be extremely useful. Known PCR assays are not practical to use in golf course or other intensively managed turf grass or professional landscape settings, as PCR requires specialised laboratory skills and instruments. Certain other molecular biology methods for decting fungal disease in turf grass are known and described, for example, in WO2009147017 which relates to a TRFLP methodology.

The present invention accordingly relates to a LAMP assay for detecting the presence of DNA in a turf sample which is associated with selected fungal pathogens that cause relevant turf diseases including, for example, anthracnose, take-all patch, summer patch, snow mold, *Pythium* blight, brown patch and dollar spot.

To facilitate timely and efficient detection of turf grass disease pathogens and to improve the cost and effectiveness of turf grass disease treatments, a LAMP assay according to the invention can be utilized to earlier detect DNA associated with fungal pathogens which cause relevant turf diseases. In accordance with the invention, the LAMP method suitably uses a primer set of at least four and preferably six or more nucleic acid sequences derived from the target disease pathogens. More particularly, the inventive method provides that each primer used in the selected primer set for the LAMP assay has from 15 to 50 nucleic acids and where the primers in the set are selected from a specific DNA loci within the target fungi.

In accordance with the present invention, a method for detecting fungal DNA in a turf grass sample with a loop-mediated isothermal amplification (LAMP) assay is provided which contains primers for fungal DNA (nucleic acids) of a turf pathogenic fungi selected from the group consisting of *Sclerotinia homoeocarpa, Rhizoctonia solani* spp., *Pythium ashanidematum, Gaeumannomyces graminis* spp., *Microdochium nivale* spp., *Magnaporthe poae, Colletotrihum graminicola, Colletotrichum cereale* and *Pytium ultimum* var. *ultimum*(target fungi). The LAMP assay of the present invention uses a primer set of at least four and preferably six or more nucleic acid sequences with each primer in the set having from 15 to 50 nucleic acids, and where the fungal DNA to be detected is obtained from a target fungal pathogen. The primers useful in the present LAMP assay method are selected from specific internal transcribed spacer regions or genes of the target fungi to provide improved assay results.

In a particular embodiment, the *Microdochium nivale* spp. target fungi are selected from *Microdochium nivale* var. *nivale* and *Microdochium nivale* var. *majus*. In another embodiment, the *Gaeumannomyces graminis* spp. target fungi are selected from *Gaeumannomyces graminis* var. *avenae, Gaeumannomyces graminis* var. *graminis* and *Gaeumannomyces graminis* var. *tritici*. In a further embodiment, the *Rhizoctonia solani* spp. target fungi are selected from *Rhizoctonia solani* AG2-2IV and *Rhizoctonia solani* AG2-2IIIB.

In the context of the present invention, detection of fungal DNA with the inventive LAMP assay in a turf sample may be indicative of the presence of fungal pathogens and can also assist in assessing the onset or presence of a turf disease condition as follows:

| Fungal Pathogen | Turf Disease |
| --- | --- |
| *Sclerotinia homoeocarpa* | Dollar Spot |
| *Rhizoctonia solani* spp. | Brown Patch |
| *Microdochium nivale* spp. | Snow Mold |
| *Pythium aphanidermatum* | Pythium Blight |
| *Gaeumannomyces graminis* spp. | Take-all patch |
| *Magnaporthe poae* | Summer patch |
| *Colletotrichum graminicola* | Anthracnose |
| *Colletotrichum cereale* | Anthracnose |
| *Pythium ultimum* | Pythium Blight |

In one embodiment, (a) the primer set for *Sclerotinia homoeocarpa* DNA is selected from within the DNA of SEQ ID NO: 1;

(b) the primer set for *Rhizoctonia solani* DNA is selected from within the DNA of SEQ ID NO: 2 or SEQ ID NO: 9;

(c) the primer set for *Microdochium nivale* spp. DNA (preferably *Microdochium nivale* var. *nivale*) is selected from within the DNA of SEQ ID NO: 3;

(d) the primer set for *Pythium ashanidematum* DNA is selected from within the DNA of SEQ ID NO: 4 or SEQ ID NO: 10;

(e) the primer set for *Gaeumannomyces graminis* spp. DNA (preferably *Gaeumannomyces graminis* var. *avenae*, *Gaeumannomyces graminis* var. *graminis* or *Gaeumannomyces graminis* var. *tritici*) is selected from within the DNA of SEQ ID NO: 5 or SEQ ID NO: 8;

(f) the primer set for *Microdochium nivale* spp. DNA (preferably *Microdochium nivale* var. *majus*) is selected from within the DNA of SEQ ID NO:6;

(g) the primer set for *Magnaporthe poae* DNA is selected from within the DNA of SEQ ID NO: 7;

(h) the primer set for *Colletotrihum graminicola* DNA is selected from within the DNA of SEQ ID NO: 11;

(i) the primer set for *Colletotrichum cereale* DNA is selected from within the DNA of SEQ ID NO: 12; and (j) the primer set for *Pytium ultimum* var. *ultimum* DNA is selected from within the DNA of SEQ ID NO: 13

Preferably the LAMP primer sets suitable for use in detecting fungi DNA in turf samples according to the present invention comprise four primers including: a pair of forward (FIP) and reverse (BIP) inner primers, and a pair of forward (F3) and reverse (B3) outer primers. More preferably, the LAMP primer sets suitable for use in the present invention include the addition of loop forward (LF) and/or loop back (LB) primers to accelerate amplification of nucleic acid present in the turf sample and to reduce the detection time of any target fungi that may be present in such turf sample. The LAMP primer set embodiments listed below relate to the detection of the target fungi DNA in turf samples in accordance with the method of the invention.

In the description of the embodiments which follow that are associated with the primers of SEQ ID Nos. 14-91 according to the invention, it will be understood that the primers useful in the present invention each independently and respectively have a sequence which is at least 90%, preferably at least 95%, more preferably at least 96%, and even more preferably at least 97% identical to the primers of SEQ IDs of 14-91.

In a particularly preferred embodiment, the primers useful in the present invention each independently and respectively have a sequence which is at least at least 98%, more preferably at least 99% identical to the primers of SEQ IDs of 14-91. Most preferably, the primers useful in the present invention each independently and respectively have a sequence which is identical to SEQ IDs of 14-91.

Accordingly, the present invention provides a method for detecting fungal DNA in a turf grass sample with a loop-mediated isothermal amplification (LAMP) assay which contains primers for fungal DNA of at least one turf pathogenic fungi selected from *Sclerotinia homoeocarpa*, *Rhizoctonia solani* spp., *Pythium ashanidematum*, *Gaeumannomyces graminis* spp., *Microdochium nivale* spp., *Magnaporthe poae*, *Colletotrihum graminicola*, *Colletotrichum cereale* and *Pytium ultimum* var. *ultimum*, comprising: subjecting the turf sample to a LAMP reaction wherein the LAMP reaction uses a primer set of four or more nucleic acid sequences with each primer in the set having from 15 to 50 nucleic acids, and wherein the set of primers comprises at least one primer set as described below.

In one embodiment, the primer set for detecting *Sclerotinia homoeocarpa* DNA comprises or is selected from SEQ ID NOs: 15 and 27.

In another embodiment, the primer set for detecting *Sclerotinia homoeocarpa* DNA comprises or is selected from SEQ ID NOs:14, 15, 16 and 17.

In a further embodiment, the primer set for detecting *Sclerotinia homoeocarpa* DNA comprises or is selected from SEQ ID NOs: 14, 15, 16, 17, 18 and 19.

In a further embodiment, the primer set for detecting *Rhizoctonia solani* DNA comprises or is selected from SEQ ID NO: 23.

In another embodiment, the primer set for detecting *Rhizoctonia solani* DNA comprises or is selected from SEQ ID Nos: 63, 64 and 65.

In another embodiment, the primer set for detecting *Rhizoctonia solani* DNA comprises or is selected from SEQ ID NO: 20, 21, 22 and 23.

In another embodiment, the primer set for detecting *Rhizoctonia solani* DNA comprises or is selected from SEQ ID NO: 62, 63. 66 and 67.

In yet another embodiment, the primer set for detecting *Rhizoctonia solani* DNA comprises or is selected from SEQ ID Nos: 62, 63, 64, 65, 66 and 67.

In another embodiment, the primer set for detecting *Rhizoctonia solani* DNA comprises or is selected from SEQ ID Nos: 20, 21, 22, 23, 24 and 25.

In another embodiment, the primer set for detecting *Microdochium nivale* spp. (preferably *Microdochium nivale* var. *nivale*) DNA comprises or is selected from SEQ ID Nos: 27, 28 and 29.

In another embodiment, the primer set for detecting *Microdochium nivale* spp. (preferably *Microdochium nivale* var. *nivale*) DNA comprises or is selected from SEQ ID NO: 26, 27, 28, and 29.

In a further embodiment, the primer set for detecting *Microdochium nivale* spp. (preferably *Microdochium nivale* var. *nivale*) DNA comprises or is selected from SEQ ID Nos: 26, 27, 28, 29, 30 and 31.

In one embodiment, the primer set for detecting *Pythium ashanidematum* DNA comprises or is selected from SEQ ID NOs:33, 36 and 37.

In another embodiment, the primer set for detecting *Pythium ashanidematum* DNA comprises or is selected from SEQ ID NO: 32, 33, 36, and 37.

In another embodiment, the primer set for detecting *Pythium ashanidematum* DNA comprises or is selected from SEQ ID NOs: 32, 33, 34, 35, 36 and 37.

In another embodiment, the primer set for detecting *Pythium ashanidematum* DNA comprises or is selected from SEQ ID NOs:69, 70 and 71.

In another embodiment, the primer set for detecting *Pythium ashanidematum* DNA comprises or is selected from SEQ ID NO: 68, 69, 72 and 73.

In another embodiment, the primer set for detecting *Pythium ashanidematum* DNA comprises or is selected from SEQ ID NOs: 68, 69, 70, 71, 72 and 73.

In one embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NO: 60.

In another embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NOs: 42 and 43.

In a further embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NO: 38, 39, 42 and 43.

In a further embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NO: 56, 57, 60 and 61.

In another embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NOs: 38, 39, 40, 41, 42 and 43.

In another embodiment, the primer set for detecting *Gaeumannomyces graminis* spp. (preferably *Gaeumannomyces graminis* var. *avenae*, *Gaeumannomyces graminis* var. *graminis* or *Gaeumannomyces graminis* var. *tritici*) DNA comprises or is selected from SEQ ID NO: 56, 57, 58, 59, 60 and 61.

In one embodiment, the primer set for detecting *Microdochium nivale* spp. (preferably *Microdochium nivale* var. *majus*) DNA comprises or is selected from SEQ ID Nos: 48 and 49.

In a further embodiment, the primer set for detecting *Microdochium nivale* spp. (preferably *Microdochium nivale* var. *majus*) DNA comprises or is selected from SEQ ID NO: 44, 45, 48 and 49.

In yet another embodiment, the primer set for detecting *Microdochium nivale* spp. (preferably *Microdochium nivale* var. *majus*) DNA comprises or is selected from SEQ ID Nos: 44, 45, 46, 47, 48 and 49.

In another embodiment, the primer set for detecting *Magnaporthe poae* DNA comprises or is selected from SEQ ID NOs: 54 and 55.

In a further embodiment, the primer set for detecting *Magnaporthe poae* DNA comprises or is selected from SEQ ID NO: 50, 51, 54 and 55.

In another embodiment, the primer set for detecting *Magnaporthe poae* DNA comprises or is selected from SEQ ID NOs: 50, 51, 52, 53, 54, and 55.

In one embodiment, the primer set for detecting *Colletotrihum graminicola* DNA comprises or is selected from SEQ ID NOs:74, 76 and 77.

In a further embodiment, the primer set for detecting *Colletotrihum graminicola* DNA comprises or is selected from SEQ ID NO: 74 75, 78 and 79.

In another embodiment, the primer set for detecting *Colletotrihum graminicola* DNA comprises or is selected from SEQ ID NOs:74, 75, 76, 77, 78 and 79.

In another embodiment, the primer set for detecting *Colletotrichum cereale* DNA comprises or is selected from SEQ ID Nos 80, 82 and 83.

In a further embodiment, the primer set for detecting *Colletotrichum cereale* DNA comprises or is selected from SEQ ID NO: 80, 81, 84 and 85.

In another embodiment, the primer set for detecting *Colletotrichum cereale* DNA comprises or is selected from SEQ ID Nos 80, 81, 82, 83, 84 and 85.

In one embodiment, the primer set for detecting *Pytium ultimum* var. *ultimum* Idin-rc DNA comprises or is selected from SEQ ID Nos: 86, 88 and 89.

In a further embodiment, the primer set for detecting *Pytium ultimum* var. *ultimum* Idin-rc DNA comprises or is selected from SEQ ID NO: 86, 87, 90 and 91.

In another embodiment, the primer set for detecting *Pytium ultimum* var. *ultimum* Idin-rc DNA comprises or is selected from SEQ ID Nos: 86, 87, 88, 89, 90 and 91.

The LAMP assays of the invention can be used for detection, including early detection, of DNA from turf fungi selected from the group consisting of *Sclerotinia homoeocarpa*, *Rhizoctonia solani*, *Pytium aphanidermatum*, *Gaeumannomyces graminis* spp., *Microdochium nivale* spp., *Magnaporthe poae*, *Colletotrihum graminicola*, *Colletotrichum cereale* and *Pytium ultimum* var. *ultimum* in turf samples which is easy to obtain and allows management and/or maintenance of the turf grass to be tailored accordingly.

According to the invention, by "turf grass" there is understood an annual or perennial Gramineae. Said gramineae preferably belongs to one or more of the genera *Agropyron, Agrostis, Axonopus, Bromus, Buchloë, Cynodon, Eremochloa, Festuca, Lolium, Paspulum, Pennisetum, Phleum, Poa, Stenotaphrum* or *Zoysia*. More preferably, said gramineae belongs to one or more of the genera *Agrostis, Buchloe, Cynodon, Eremochloa, Festuca, Lolium, Paspulum, Pennisetum, Poa, Stenotaphrum* or *Zoysia*.

In one embodiment, according to the invention by "turf" is understood as a group of turf grass, which covers a surface area of ground and is subject to regular maintenance.

The present invention can be practiced with all turf grasses, including cool season turf grass and warm season turf grass.

Examples of cool season turf grasses are: Bluegrasses (*Poa* L.), such as Kentucky Bluegrass (*Poa pratensis* L.), Rough Bluegrass (*Poa trivialis* L.), Canada Bluegrass (*Poa compressa* L.) and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.); Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia*), Tall Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); Wheatgrasses (*Agropyron* Gaertn.), such as Fairway Wheatgrass (*Agropyron cristatum* (L.) Gaertn.), Western Wheatgrass (*Agropyron smithii* Rydb.). Other cool season turf grasses include Smooth Brome (*Bromus inermis* Leyss.) and Timothy Phleum L.).

Examples of warm season turf grasses are Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (*Eremochloa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.) and Seashore *Paspalum* (*Paspalum vaginatum* swartz).

The LAMP method invention also contemplates a kit for the detection of fungi in a turf grass sample using a LAMP assay. A test strip containing one or more than one of the primer sets as described herein can be utilized. In one embodiment, multiple primer sets are multiplexed on a test strip for the detection of multiple diseases from turf grass samples collected from a particular locus.

For example, a bijou tube with a ball bearing and a suitable amount of lysis buffer is provided with a 1 cubic cm homogenized turf sample and shaken vigorously for 1 minute. A test strip with sample well containing all the resuspension buffer and drops of this test solution are placed into a sample wells on a test strip wherein the wells have all the ingredients necessary to perform a LAMP reaction (e.g., the primer sets and a reagent such as an isothermal master mix cat no. iso-001 available from Optigene). In one embodiment, the test strips are multiplexed. In another embodiment, the test strip includes 8 wells, two control and 6 for turf diseases of interest. In one embodiment, the test strip is associated with a diagnostic instrument such as a Genie® II or III available from OptiGene.

Primer Design

Highly conserved genes were used for the design of the LAMP primers for the detection of DNA from selected turf grass pathogens (column 1 of TABLE 3). Pure genomic DNA from all fungi of interest was obtained using the NucleoSpin Plant II (MACHEREY-NAGEL). With PCR technology the sequence of interest were amplified using published primer pairs followed by a Sanger sequencing. The following DNA Loci (genes and regions) were sequenced: Internal transcribed spacer (ITS), elongation factor 1-alpha (EF), beta-tubulin (Tub), cytochrome c oxidase subunit 1 (Cox), superoxide dismutase (SOD1) and large subunit nuclear ribosomal RNA (LSU). The raw sequences were aligned using ClustalW alignment method (CLC Main Workbench Software). The BLAST comparisons with sequences from GenBank (NCBI) were used to identify gene homologs. Ideally, a good sequence is defined by successful PCR amplification for all target taxa and no homology with other taxa.

The best sequences (SEQ ID Nos, 1-13) from the sequenced DNA Loci were then used for the design of the LAMP primers for each of the selected turf grass pathogens using LAMP Designer 1.14 (PREMIER Biosoft). Therefore different parameters were tested to get different primer sets per organisms and loci (See TABLE 3 for a correlation of turf pathogen, selected loci and SEQ ID of best sequences used for primer design). The designed primers sets shown in TABLE 1 were then tested for their specificity (TABLE 3) and sensitivity (TABLE 4).

TABLE 1

| DNA SEQ ID (Primer Sets) | Primer SEQ ID NO. | Primer name |
|---|---|---|
| 1 | 14 | B3 |
|  | 15 | BIP |
|  | 16 | F3 |
|  | 17 | FIP |
|  | 18 | LB |
|  | 19 | LF |
| 2 | 20 | B3 |
|  | 21 | BIP |
|  | 22 | F3 |
|  | 23 | FIP |
|  | 24 | LB |
|  | 25 | LF |
| 3 | 26 | B3 |
|  | 27 | BIP |
|  | 28 | F3 |
|  | 29 | FIP |
|  | 30 | LB |
|  | 31 | LF |
| 4 | 32 | F3 |
|  | 33 | B3 |
|  | 34 | LF |
|  | 35 | LB |
|  | 36 | FIP |
|  | 37 | BIP |
| 5 | 38 | F3 |
|  | 39 | B3 |
|  | 40 | LF |

TABLE 1-continued

| DNA SEQ ID (Primer Sets) | Primer SEQ ID NO. | Primer name |
|---|---|---|
|  | 41 | LB |
|  | 42 | FIP |
|  | 43 | BIP |
| 6 | 44 | F3 |
|  | 45 | B3 |
|  | 46 | LF |
|  | 47 | LB |
|  | 48 | FIP |
|  | 49 | BIP |
| 7 | 50 | F3 |
|  | 51 | B3 |
|  | 52 | LF |
|  | 53 | LB |
|  | 54 | FIP |
|  | 55 | BIP |
| 8 | 56 | F3 |
|  | 57 | B3 |
|  | 58 | LF |
|  | 59 | LB |
|  | 60 | FIP |
|  | 61 | BIP |
| 9 | 62 | F3 |
|  | 63 | B3 |
|  | 64 | LF |
|  | 65 | LB |
|  | 66 | FIP |
|  | 67 | BIP |
| 10 | 68 | F3 |
|  | 69 | B3 |
|  | 70 | LF |
|  | 71 | LB |
|  | 72 | FIP |
|  | 73 | BIP |
| 11 | 74 | F3 |
|  | 75 | B3 |
|  | 76 | LF |
|  | 77 | LB |
|  | 78 | FIP |
|  | 79 | BIP |
| 12 | 80 | F3 |
|  | 81 | B3 |
|  | 82 | LF |
|  | 83 | LB |
|  | 84 | FIP |
|  | 85 | BIP |
| 13 | 86 | F3 |
|  | 87 | B3 |
|  | 88 | LF |
|  | 89 | LB |
|  | 90 | FIP |
|  | 91 | BIP |

Specificity

To examine the specificity of the reaction (Literature see below), assays using the designed primer sets are tested using pure genomic DNA extracts from the fungal isolates described in TABLE 2. A comprehensive collection of different turf grass pathogens from distinct geographical origins were collected and grow on different media (potato dextrose/malt/cornmeal/cherry/V8). A ten-day old fungal culture was used to extract the DNA from mycelium (NucleoSpin Plant II—MACHEREY-NAGEL). The genomic DNA was diluted with nuclease free water to 5 ng/µl and a portion of 2.5 µl was used for the specificity tests.

The LAMP specificity tests were performed on a Light-Cycler 480 (Roche) in 96 well plates at 64° C. for 55 min. The amplicon-specific annealing temperature was determined during cooling from 98° C. to 65° C. with a ramp rate of −0.1° C. per second. Real-time LAMP assays were carried out in 10 µl reaction mixtures containing 5 µl of isothermal master mix at a 1× concentration (Optigene), 0.4

µM each external primer, 1.6 µM each internal primer, and 0.8 µM each loop primer (synthesized by Microsynth) and 2.5 µl of genomic DNA.

All reactions were carried out in duplicate and at two different days.

Literature for performing specificity:

Besuschio, S. A., Murcia, M. L., Benatar, A. F., Monnerat, S., Cruz, I., Picado, A., Schijman, A. G. (2017). Analytical sensitivity and specificity of a loop-mediated isothermal amplification (LAMP) kit prototype for detection of *Trypanosoma cruzi* DNA in human blood samples. PLOS Neglected Tropical Diseases, 11(7), e0005779.

Kitamura, M., Aragane, M., Nakamura, K., Watanabe, K., & Sasaki, Y. (2016). Development of Loop-Mediated Isothermal Amplification (LAMP) Assay for Rapid Detection of *Cannabis sativa*. Biological and Pharmaceutical Bulletin, 39(7), 1144-1149.

Seki, M., Kilgore, P. E., Kim, E. J., Ohnishi, M., Hayakawa, S., & Kim, D. W. (2018). Loop-Mediated Isothermal Amplification Methods for Diagnosis of Bacterial Meningitis. Frontiers in Pediatrics, 6.

Wang, D.-G., Brewster, J. D., Paul, M., & Tomasula, P. M. (2015). Two Methods for Increased Specificity and Sensitivity in Loop-Mediated Isothermal Amplification. Molecules, 20(4), 6048-6059.

TABLE 2

| ID | Microorganism | Strain number |
|---|---|---|
| 1 | *Colletotrichum cereale* | Stein 13-421 |
| 2 | *Colletotrichum cereale* | Stein UKCC1 |
| 3 | *Colletotrichum cereale* | Stein 13-394 |
| 4 | *Colletotrichum cereale* | Stein 13-396 |
| 5 | *Colletotrichum cereale* | Stein 13-415 |
| 6 | *Colletotrichum cereale* | Stein 871 |
| 7 | *Colletotrichum graminicola* | CBS 113173 |
| 8 | *Colletotrichum graminicola* | CBS 130836 |
| 9 | *Gaeumannomyces graminis* | Stein 870 |
| 10 | *Gaeumannomyces graminis* var. *avenae* | CBS 187.65 |
| 11 | *Gaeumannomyces graminis* var. *avenae* | Stein 880 |
| 12 | *Gaeumannomyces graminis* var. *avenae* | CBS 870.73 |
| 13 | *Gaeumannomyces graminis* var. *graminis* | CBS 387.81 |
| 14 | *Gaeumannomyces graminis* var. *graminis* | CBS 235.32 |
| 15 | *Gaeumannomyces graminis* var. *graminis* | CBS 903.73 |
| 16 | *Gaeumannomyces graminis* var. *tritici* | Stein 334 |
| 17 | *Gaeumannomyces graminis* var. *tritici* | CBS 186.65 |
| 18 | *Gaeumannomyces graminis* var. *tritici* | CBS 247.29 |
| 19 | *Magnaporthe poae* | CBS 131396 |
| 20 | *Magnaporthe poae* | CBS 131395 |
| 21 | *Microdochium nivale majus* | Stein 529 |
| 22 | *Microdochium nivale nivale* | Stein 72 |
| 23 | *Microdochium nivale* var. *nivale* | Stein 868 |
| 24 | *Microdochium nivale* var. *nivale* | Stein UKMN1 |
| 25 | *Microdochium nivale* var. *nivale* | Stein MN12055 |
| 26 | *Pythium aphanidermatum* | CBS 164.68 |
| 27 | *Pythium aphanidermatum* | Stein 889 |

TABLE 2-continued

| ID | Microorganism | Strain number |
|---|---|---|
| 28 | *Pythium aphanidermatum* | Stein K5902 |
| 29 | *Pythium aphanidermatum* | Stein 186 |
| 30 | *Pythium aphanidermatum* | Stein K6179 |
| 31 | *Pythium aphanidermatum* | Stein 620 |
| 32 | *Pythium ultimum* | CBS 122650 |
| 33 | *Pythium ultimum* var. *sporangiiferum* | CBS 219.65 |
| 34 | *Pythium ultimum* var. *ultimum* | CBS 305.35 |
| 35 | *Pythium ultimum* var. *ultimum* | Stein 71 |
| 36 | *Pythium ultimum* var. *ultimum* | Stein 146 |
| 37 | *Pythium ultimum* var. *ultimum* | CBS 378.34 |
| 38 | *Pythium ultimum* var. *ultimum* | CBS 725.94 |
| 39 | *Pythium ultimum* var. *ultimum* | CBS 726.94 |
| 40 | *Pythium ultimum* var. *ultimum* | Stein K6772 |
| 41 | *Pythium ultimum* var. *ultimum* | Stein K6773 |
| 42 | *Rhizoctonia solani* AG1.1C | CBS 109195 |
| 43 | *Rhizoctonia solani* AG2-2IV | CBS 109196 |
| 44 | *Rhizoctonia solani* AG4 | CBS 253.29 |
| 45 | *Rhizoctonia solani* AG | Stein 160 |
| 46 | *Rhizoctonia solani* AG2-2IIIB | Stein 722 |
| 47 | *Rhizoctonia solani* AG1-1A | Stein 184 |
| 48 | *Rhizoctonia solani* AG1-1 | ZHAW 103 |
| 49 | *Rhizoctonia solani* AG1-1A | CBS 101759 |
| 50 | *Rhizoctonia solani* AG1-1B | CBS 101761 |
| 51 | *Rhizoctonia solani* AG1-1C | CBS 101762 |
| 52 | *Rhizoctonia solani* AG1-1A | CBS 205.84 |
| 53 | *Rhizoctonia solani* AG1-1B | CBS 324.84 |
| 54 | *Rhizoctonia solani* AG2-2IIIB | CBS 101765 |
| 55 | *Rhizoctonia solani* AG4 | CBS 319.33 |
| 56 | *Sclerotinia homoeocarpa* | CBS 510.89 |
| 57 | *Sclerotinia homoeocarpa* | Stein 867 |
| 58 | *Sclerotinia homoeocarpa* | Stein 869 |
| 59 | *Sclerotinia homoeocarpa* | Stein UKSH1 |
| 60 | *Sclerotinia homoeocarpa* | Stein UKSH2 |
| 61 | *Sclerotinia homoeocarpa* | Stein UKSH3 |
| 62 | *Sclerotinia homoeocarpa* | Stein 13-392 |
| 63 | *Sclerotinia homoeocarpa* | Stein 13-410 |
| 64 | *Sclerotinia homoeocarpa* | Stein S-9 |
| 65 | *Sclerotinia homoeocarpa* | Stein S-83 |
| 66 | *Thanatephorus cucumeris/Rhizoctonia solani* AG3 | CBS 251.31 |
| 67 | *Thanatephorus cucumeris/Rhizoctonia solani* AG2-2IIIB | SYN 866 |
| 68 | *Thanatephorus cucumeris/Rhizoctonia solani* AG1-1A | Stein 184 |
| 69 | *Thanatephorus cucumeris/Rhizoctonia solani* AG4 | Stein 689 |

Stein and SYN strains: Syngenta, CH-4332 Stein, Switzerland
CBS strains: Westerdijk Fungal Biodiversity Institute, Utrecht, The Netherlands
ZHAW strains: Zurich University of Applied Sciences, Postfach 8820, Wädenswil, Switzerland Interpretation of the results:

As summarized in TABLE 3, the specificity of the LAMP assay was checked against the designed specific target for the fungi strains listed in TABLE 2. As an additional confirmation of specificity, a matching melting temperature of 82.6-89.9° C.±0.5° C. was observed for the different amplified products as also shown in TABLE 3.

TABLE 3

| Turf Grass Pathogen | DNA Loci | DNA of SEQ ID NO. | Primer set (Table 1) | Tm +/−0.5° C. (melting temperature) | Positive reaction with organisms (Table 2) |
|---|---|---|---|---|---|
| *Sclerotinia homoeocarpa* | Elongation factor 1-alpha | 1 | 1 | 87.1 | 56-65 |
| *Rhizoctonia solani* AG2-2IIIB | Internal Transcribed Spacer | 2 | 2 | 86.0 | 43, 46, 48, 54, 55, 67 |
| *Rhizoctonia solani* AG2-2IV | Beta-Tubulin | 9 | 9 | 89.9 | 43 |
| *Microdochium nivale* var. *nivale* | Beta-Tubulin | 3 | 3 | 88.9 | 22-25 |
| *Pythium aphanidermatum* | Beta-Tubulin | 4 | 4 | 89.3 | 26-31 |
| *Pythium aphanidermatum* | Cytochrome c oxidase subunit 1 | 10 | 10 | 82.6 | 26-31, 32-33 |
| *Gaeumannomyces graminis* var. *Avenae* | Beta-Tubulin | 5 | 5 | 89.7 | 10-18 |

TABLE 3-continued

| Turf Grass Pathogen | DNA Loci | DNA of SEQ ID NO. | Primer set (Table 1) | Tm +/−0.5° C. (melting temperature) | Positive reaction with organisms (Table 2) |
|---|---|---|---|---|---|
| *Gaeumannomyces graminis* var. *Avenae* | Beta-Tubulin | 8 | 8 | 88.2 | 10-18 |
| *Microdochium nivale* var. *majus* | Beta-Tubulin | 6 | 6 | 89.2 | 21 |
| *Magnaporthe poae* | Beta-Tubulin | 7 | 7 | 88.4 | 19-20 |
| *Colletotrichum graminicola* | Superoxide Dismutase | 11 | 11 | 88.9 | 7-8 |
| *Colletotrichum cereale* | Superoxide Dismutase | 12 | 12 | 89.6 | 2-6 |
| *Pythium ultimum* var. *ultimum* | Large Subunit Nuclear Ribosomal RNA | 13 | 13 | 88.8 | 33-41 |

The sensitivity of the of the described primer sets corresponding to the DNA of Seq ID Nos. 1-13 (Table 1) were determined using serial dilutions of genomic DNA (1 ng to 100 fg) of all fungi of interests, with each reaction made in duplicate at two different days. Pure genomic DNA from all fungi was obtained using the NucleoSpin Plant II (MACHEREY-NAGEL). The LAMP sensitivity tests were performed on a LightCycler 480 (Roche) in 96 well plates at 64° C. for 55 min. The amplicon-specific annealing temperature was determined during cooling from 98° C. to 65° C. with a ramp rate of −0.1° C. per second. Real-time LAMP assays were carried out in 10 μl reaction mixtures containing 5 μl of isothermal master mix at a 1× concentration (Optigene), 0.4 μM each external primer, 1.6 μM each internal primer, and 0.8 μM each loop primer (synthesized by Microsynth) and 2.5 μl of genomic DNA.

TABLE 4

| DNA of SEQ ID NO. | Tm +/−0.5° C. (melting temperature) | Sensitivity/detection limit of genomic DNA |
|---|---|---|
| 1 | 87.1 | 2.5 picogram |
| 2 | 86.0 | 2.5 picogram |
| 3 | 88.9 | 250 picogram |
| 4 | 89.3 | 25 picogram |
| 5 | 89.7 | 25 picogram |
| 6 | 89.2 | 25 picogram |
| 7 | 88.4 | 25 picogram |
| 8 | 88.2 | 2.5 picogram |
| 9 | 89.9 | 250 picogram |
| 10 | 82.6 | 25 picogram |
| 11 | 88.9 | 25 picogram |
| 12 | 89.6 | 25 picogram |
| 13 | 88.8 | 2.5 picogram |

Method of Detecting Fungal Pathogen in a Turf Grass Sample

Sample Collection

A tuft of turf sample including grass roots is collected at a location where a fungal pathogen is expected. The turfgrass may also show symptoms. The turf sample is placed in a clean 50 ml tube (Corning) and stored at −20° C. until use. DNA is extracted using Plant Material Lysis Kit (Optigene). A 1 cm$^3$ cube of the turf sample is placed into a Bijou tube containing 1 ml of lysis buffer (Optigene). The homogenization of the turf sample is conducted by shaking the Bijou tube for 1 min. A volume of 10 μl of the lysate is transferred into a dilution tube provided (Optigene) and mixed vigorously by shaking. The diluted lysate is subsequently defined as the template.

LAMP Reaction

In some embodiments, the LAMP reaction is performed at about 60° C. to about 70° C., such as about 64° C. to about 67° C., or about 64° C. to about 66° C. In specific examples, the LAMP reaction is performed at 64° C.

In some embodiments, the LAMP reaction is allowed to proceed for about 15 to about 45 minutes, such as about 20 minutes to about 40 minutes, or about 25 minutes to about 35 minutes.

In some embodiments, the concentration of primers in the LAMP reaction according to the present invention is 1.4-1.8 μM, more specifically 1.6 μM for the forward (FIP) and reverse (BIP) inner primers, 0.2-0.4 μM, more specifically 0.4 μM for forward (F3) and reverse (B3) outer primers, and 0.4-0.8 μM, more specifically 0.8 μM, loop forward (LF) and/or loop back (LB) primers that are useful to accelerate amplification of nucleic acid present in the turf sample and to reduce the detection time of any target fungi DNA that may be present in such turf sample.

Suitable buffer systems useful in the reaction of LAMP assay include:

1× Isothermal Amplification Buffer Pack from New England Biolabs
    20 mM Tris-HCl
    10 mM $(NH_4)_2SO_4$
    50 mM KCl
    2 mM $MgSO_4$
    0.1% Tween® 20
    (pH 8.8 @ 25° C.)

1× Isothermal Amplification Buffer II Pack from New England Biolabs
    20 mM Tris-HCl
    10 mM $(NH_4)_2SO_4$
    150 mM KCl
    2 mM $MgSO_4$
    0.1% Tween® 20
    (pH 8.8@ 25° C.)

Suitable enzyme systems (DNA polymerase, etc.) useful in the reaction of LAMP assay include:

| Distributor | catalog | Product name |
|---|---|---|
| New England Biolabs | M0374 | Bst 3.0 DNA Polymerase |
| New England Biolabs | M0537 | Bst 2.0 DNA Polymerase |
| New England Biolabs | M0538 | Bst 2.0 WarmStart ® DNA Polymerase |
| New England Biolabs | M0275 | Bst DNA Polymerase, Large Fragment |
| Lucigen | 30066 | LavaLAMP ™ DNA Master Mix |
| Lucigen | 30067 | LavaLAMP ™ DNA Master Mix with Dye |
| Eiken | LMP204 | DNA Amplification Kit |
| Eiken | LMP207 | Dried DNA Amplification Reagent |

-continued

| Distributor | catalog | Product name |
|---|---|---|
| Optigene | ISO-001 | FAST isothermal amplification with dye |
| Optigene | ISO-001nd | FAST isothermal amplification |
| Optigene | ISO-DR001 | FAST isothermal amplification with dye, dried |
| Optigene | ISO-004 | FASTEST isothermal amplification with dye |
| Optigene | ISO-004nd | FASTEST isothermal amplification |
| Optigene | ISO-DR004 | FASTEST isothermal amplification with dye, dried |
| Optigene | ISO-001Tin | HIGHLY THERMOSTABLE enzyme suitable for isothermal amplification with dye |
| Optigene | ISO-DR001Tin | HIGHLY THERMOSTABLE enzyme suitable for isothermal amplification with dye, dried |

In one embodiment, the LAMP reactions are performed on a Genie instrument (Optigene) in a test strip with dried reagents (Optigene). In one embodiment, the strips have eight 150 μl wells (2 control and 6 for assays). Real-time LAMP assays are carried out in 25 μl reaction mixtures containing 15 μl of isothermal master mix at a 1× concentration (Optigene), 0.4 μM each external primer, 1.6 μM each internal primer, and 0.8 μM each loop primer (synthesized by Microsynth) selected from at least one of the primer sets of Table 1. Prior to adding the template, the lyophilized reaction strip is resuspended in 22 μl resuspension buffer (Optigene). All test strips include a negative control and a positive plant control primer set provided by Optigene. For all assays, 3 μl of template is added per reaction and well. The reaction is held at 64° C. for 30-55 min followed by an anneal program. The temperature profile of the anneal program is determined during cooling from 98° C. to 65° C. with a ramp rate of −0.1° C. per second.

The isothermal master mix contains a fluorescent double-stranded DNA binding dye to permit the real-time detection of the amplicons. The assays are optimized in terms of reaction time, temperature, and the volume of DNA added per reaction.

The fluorescence data that is acquired during amplification phase at 64° C. is reported as amplification time. The fluorescence derivative data that is acquired during the anneal phase is reported as an annealing temperature.

Alternatively, the LAMP assay reaction does not include an anneal program in which case a pH-sensitive indicator dye can be used to assess the presence of target fungal DNA. In some examples, the pH-sensitive indicator dye is a colored dye detectable in visible light. In particular examples, the colored dye comprises cresol red, phenol red, m-cresol purple, bromocresol purple, neutral red, naphtholphthalein, thymol blue or naphtolphthalein. In other examples, the pH-sensitive indicator dye is a fluorescent indicator dye. In particular examples, the fluorescent dye comprises 2',7'-bis-(2-carboxyethyl)-5(6)-carboxyfluorescein, 5(6)-carboxy-2',7'-dichlorofluorescein, 5(6)-carboxyfluorescein, 3,6-diacetoxyphthalonitrile, 6,8-dihydroxy-1,3-pyrenedisulfonic acid, or 5-(and-6)-carboxyl seminaphthorhodafluor.

Following the foregoing procedures, the detection of the presence of fungal pathogen DNA (Table 3) in a turf sample may indicate the presence of a turf fungal pathogen that may cause relevant turf diseases (including, for example, anthracnose, take-all patch, summer patch, snow mold, *Pythium* blight, brown patch and dollar spot). Early and efficient detection provides suitable turf grass disease management decisions to be undertaken.

SEQUENCE LISTING

```
<210>  1
<211>  912
<212>  DNA
<213>  Sclerotinia homoeocarpa

<400>  1
tagatctaca catggttctt acattatatt taggtcactt gatctacaag tgcggtggaa    60
ttgacaagcg tactattgaa aagttcgaga cggtatgact tctccacctt tctcttgcta   120
tcttttcccg tccttctcat cgagatcagt gtctgcgatc ttggtgctga tggatttatc   180
gggttgcgtt ttctctcatg cgcggagcat acatccgaat tctcaaccct ttgaacatta   240
ccacattgcc tttccagaat cccctttgcta acccgttaat aggaagccaa ggagatggga   300
aagggttcct tcaagtacgc atgggttttg gacaagttga aggctgagcg tgagcgtggt   360
atcaccatcg acattgccct ctggaagttc gagacaccta agtacaatgt tactgtcatt   420
ggtatgtgta cgaattcttt atgccaactg aagtatatta acccattcgc agatgccccc   480
ggtcatcgtg atttcatcaa gaacatgatc actggtacct cccaagctga ttgtgccatt   540
cttatcatcg ctgccggtgt tggtgagttc gaggctggta tctccaagga tggtcagacc   600
cgtgagcacg ctcttcttgc gtacactctt ggtgttaagc aacttatcgt tgccatcaac   660
aagatggaca ccaccaagtg gtccaaggat cgtttcgagg aaatcatcaa ggagacaacc   720
aacttcatca agaaggttgg ctacaacgcc aagactgttc ccttcgtgcc gatctctgga   780
ttcgagggtg ataacatgat tgagccctca actaactgcc catggtacaa gggctgggag   840
agagagtcca aggagtctgg caaacacacc ggcaagaccc ttcttgaggc catcgacagc   900
atggacctgc ct                                                       912

<210>  2
<211>  629
<212>  DNA
<213>  Rhizoctonia solani AG2-2111B

<400>  2
tgtagctggc tccattagtt tggagcatgt gcacaccttt tgctcttttt ttaatccaca    60
cacacctgtg aacctgtgag gcagagacat ggatgggaga acttttattt acttaaaat   120
gaatgattgg gacccctacc ccccccccc tctgtctact caactctaat ataaacccaa   180
tttattttaa aatgaatgta atggatgtaa cgcatctaat actaagtttc aacaacggat   240
ctcttggctc tcgcatcgat gaagaacgca gcgaaatgcg ataagtaatg tgaattgcag   300
aattcagtga atcatcgaat ctttgaacgc accttgcgct ccttggtatt ccttggagca   360
```

-continued

```
tgcctgtttg agtatcatga aatcttcaaa gtaaaccttt ttgttaactc aatttggttt    420
cactttggta ttggaggttc ttgcagcttc acacgctgct cctctttgtt cattagctgg    480
atctcagtgt tatgcttggt tcctctcggc gtgataaatt atctatcgct gaggactccc    540
gataaaaagg ttggccaagg taaatgcaga tgaaccgctt ctaatagtcc attgacttgg    600
acaataaaat aattattatt ttacgatct                                      629

<210>  3
<211> 613
<212> DNA
<213> Microdochium nivale var. nivale

<400>  3
ggtaaccaaa tcggtgctgc tttctggtgc gtacacctcg actcgaagac gaccacgacc     60
ttcgcgacga aatgaactc ggcagccaaa accgtgccg tcgagaatct ttagtcgcag     120
aggaatctaa cataagggtg gagaccggca aggctaacac tatcttccct gatacaggca    180
gaccatctcc ggcgagcacg gtcttgacga cgatggagtg taagttcaat aaccgactcg    240
cagttccttg cgagagaccg cttccctgac ggcttctcgg gccagatgaa atgcaacagt    300
actgacattc tgccaatagc tacaacggca actctgagct ccagctcgag cgcatgagcg    360
tctacttcaa cgaggtatgt caccatgggc gacttcgggc ttcacacatt cggccagcta    420
ctaactgacc acccacataa cttaggcttc cggcaacaag tacgttcccc gcgccgtcct    480
cgtcgatctc gagcccggta ccatggatgc cgtccgtgct ggtcccttcg gccagctgtt    540
ccgtcccgac aacttcgtct tcggtcagtc cggtgctggc aacaattggg ccaagggtca    600
ctacactgag ggt                                                       613

<210>  4
<211> 455
<212> DNA
<213> Pythium aphanidermatum

<400>  4
cttcagtgaa ctccatctcg tccataccct caccagtgta ccagtgcaag aaggccttac     60
gacggaacat ggccgtgaac tgctcgctga cacgcttgaa catctcctgg atggcagtcg    120
agttaccgat gaacgtggcg ctcatcttga gaccctttgg tgggatgtca caaacgctgg    180
ccttgatgtt gttcgggatc cactcaacga agtacgacga gttcttgttc tgaacgttga    240
gcatctgctc gtcgacctcc ttggtgctca tacgaccacg gaacatacaa gcggcggtca    300
ggtaacgacc gtgacgagga tcagcggcac acatcatgtt cttggcgtcg aactgctgct    360
gggtcagctc tggcaccgta agggcacggt actgctgcga gccgcgcgag gtgagcggag    420
cgaaaccgac catgaagaag tggaacgggg gaaaa                               455

<210>  5
<211> 518
<212> DNA
<213> Gaeumannomyces graminis var. avenae

<400>  5
ttagtgaccc ttggcccagt tgttgccagc accagactgg ccgaaaacga agttgtcggg     60
gcggaacagc tggccgaagg gaccggcacg aacggcgtcc atggtgccgg gctcgagatc    120
gacgaggacg gcacggggga catgcttgtt gccggaggcc tggagcggaa aggttatggg    180
tcagaataca tgatacgaag gtgggaaata ccggctgcta atgccggaca gaagcttcaa    240
ctcagggcct gtctgcatac ctcgttgaag tagacgctca tgcgctcgag ctggagctcc    300
gaggtgccgt tgtacctgta tcaatatgtc agagcggtga acggacggcg ggccgagcca    360
caagcaggac gaaatacgta cacgccattg ctgtcgagac cgtgctcgct agaaatggtc    420
tgcctgtcaa agaagtcagt acgggtcacg ggcagtggca gtcgtggtcg gcggcggatc    480
gtcgcgcggc gtcgtttcat accagaaagc agcaccgt                            518

<210>  6
<211> 550
<212> DNA
<213> Microdochium nivale var. majus

<400>  6
ggtaaccaaa tcggtgctgc tttctggtgc gtacaactcc gatactcaac gacggccgca     60
gtgacctttg cgacgaaaac aaactcggcg tcaaacccgt atcgccgaa aatcttcggt    120
cgcagaggaa tctggcaaaa gggtggaaat aaacaaggca ggctaacact ctcttcccccg    180
acacaggcaa accatctcca gtgagcacgg tctcgacagc aatggcgtgt aagttcaata    240
accgactcgc acttcttgcg aaaggccact tccctgatgg cgtatcacgc cagatgaaat    300
acacaagtac tgcatcctg tcaatagcta caacggcacc tccagctccc agctcgagcg    360
catgagtgtc tacttcaatg aggcttccgg caacaagtac gttcctcgtg ccgtccttgt    420
cgatctcgag cccggtacca tggatgccgt ccgtgctggt cccttcggcc agctgttccg    480
ccccgacaac ttcgtcttcg gtcagtccgg tgctggcaac aactgggcca agggtcacta    540
cactgagggt                                                           550
```

SEQUENCE LISTING

```
<210>  7
<211>  485
<212>  DNA
<213>  Magnaporthe poae

<400>  7
ttagtgaccc ttggcccagt tgttgccagc accggactgg ccgaaaacga agttgtcggg     60
gcggaacagc tggccgaagg gaccagcacg gacagcatcc atggtgccgg gctcgagatc    120
gaccaggacg gcacggggga catgcttgtt gccggaggcc tagagcgcgg ggaggcaatg    180
gtgtcagaaa acaacacgt ggttgcgaaa gagagacgcg ttcggagtct atctgcatac    240
ctcgttgaag tagacgctca tgcgctcgag ctggagctcc gaggtaccgt tgtaactgca    300
ccaatatgtc agagcggtga acggacatgt ggccgaggat ctcccaaaca gaatacatac    360
actccattgc tgtcgagacc gtgctcgctg gagatggttt gcctgcccag gaagtcagta    420
tcaatgatga atgatcacgg tcgtggtggg tgcgagcggt ggttcgtacc agaaagcagc    480
accgt                                                                485

<210>  8
<211>  539
<212>  DNA
<213>  Gaeumannomyces graminis var. avenae

<400>  8
cctcagtgaa ctccatctcg tccatacctc cgccagtgta ccaatgaagg aaagccttgc     60
gcctgaacat ggcagtgaac tgctcaccaa cacgcttgaa gagctcttgt atggcagtcg    120
agtttccgat gaaggtcgac gacatcttca ggccccgggg agggattgag cagagggcgg    180
tctggatgtt gttgggaatc cactcgacga agtacgacga gttcttgttc tggatgttgc    240
gcatctggtc ctcgacctcc ttcatggaga ccttaccacg gctatcgcac acagggatgg    300
ttagttagtg ccttctaggt tgggcatatt aaatgggcca gataaataag cccaatgcct    360
agatgcaaga ctcacaaaat agcagagcag gtcaggtagc gaccgttgcg gaagtccgag    420
gcagccatca tgttcttggg gtcgaacatc tgctgggtca actcgggcac cgtgacggcg    480
cggaatgagt gggcgccgcg gctagtcagg ggagcgaagc cgaccatgaa gaagtggag     539

<210>  9
<211>  236
<212>  DNA
<213>  Rhizoctonia solani AG2-21V

<400>  9
gttgtagggc tcaacaaccg tgtcggagac cttgggggaa ggaacgaccg agaatgtgca     60
catcatacga tcggggtatt cttcacggat cttggagatc aaaagggtgc ccataccggc    120
accggttcct ccaccgagcg agtgggtaat ctggaagccc tgaagacact cgcatccctc    180
ggcctctttg cgcgcgacat cgagaactgc gtcaacaagc tcggcacctt cggtgt        236

<210>  10
<211>  604
<212>  DNA
<213>  Pythium aphanidermatum

<400>  10
tgcttttca ggtgtagttg gtacaacttt atctgtttta attagaatgg aattagcaca      60
acctggtaat caaatttta tgggaaatca tcaattatat aatgttgttg taacagcaca    120
tgcttttata atgattttct tcatggttat gcctgtatta attggtggtt ttggtaactg    180
gtttattcct ttaatgattg gtgctccaga tatggctttt cctagaatga ataaatattag   240
tttttggtta ttacctcctt cattattatt attagtatca tctgctatag tagaatcagg    300
tgctggtaca ggttggactg tatatccacc attatcaagt gtacaagcac actcaggacc    360
ttcagtagat ttagctattt ttagtttaca tttatctggt atttcttcat tattaggtgc    420
tattaatttt ttatcaacta tttataatat gagagctcct ggattaagtt ttcataggtt    480
gccattattt gtttggtctg tttttattac agcttttta ttattgttaa cattaccagt     540
attagcaggt gctattacaa tgttattaac agatagaaat ttaaatactt cttttatga    600
tcct                                                                 604

<210>  11
<211>  657
<212>  DNA
<213>  Colletotrichum graminicola

<400>  11
aatattctcg acatatgcag cctttccgtt gagatactat gtacgatcac tgttagcatc     60
tcttttcaaa aaaggtcttg ttggtgtcca cgaacctgaa ggtagtacgc gtgctcccac    120
atgtcaatac caaagatggg cacgcccttg tgacagggt cctggtcttt cgtcgtgata    180
atgctgaggc ccgttatgtc atccttaaca agccaccccc agccgctacc ggtgataccc    240
agcagcgtgg tgttgaaagc ctgcttgaac tggtcgagcc cgcccagac gcgggtgatc    300
tcggcgacga gctttggcgc cgcatcgggc gaggcatcac cgctcgaggc tggggaaagg    360
ttctcccaga ataggggaatg gttgatgtgg ccgccgccgt tgaagtttag ggccgcgagg    420
acggcgatgc gattctggag cgggtttgca ttgtaagtct cgatggcctt gttcagattt    480
gtaacgtatg cttgatggct gtaggtggct tcatgtcaac tctcttcttc gctgcttcat    540
```

SEQUENCE LISTING

```
atttcatggt tatctcactg tttgctgtgg tgcagctcca tgatctgagc tgagatgtga    600
ggctcgaggg cctgcaggag gggtcagcgg gcgcgatcgc gagcacgagt aagggat       657
```

<210> 12
<211> 663
<212> DNA
<213> *Colletotrichum cereale*

<400> 12
```
cgttccagat gttctcgacg tacgccgctt ttccattgag gtactgaggc cgagcattgt     60
tagtaccttc caacaaagca gatccgtcag tgtttacgaa cctggaggta gtacgcgtgc    120
tcccacatgt ccacgccgaa gatgggcacg cccttggtga cagggtcctg gtctttcgtc    180
gtgatgatgc tcagacccgt tacgtcgtcc ttgaccagcc atcccagcc gctgccggtg     240
atacccagaa gcgtggcgtt gaaagcctgc ttgaactggt cgagcccgcc ccagacccgg    300
gcgatctcag cgacgagctt cggcgcggcg tctggcgagg cgtctgggct cgaggcaggg    360
gacaggtttt cccagaagag ggagtggttg atgtggccgc cgccgttgaa gttgagggct    420
ggaggacgg cgatgcggtt ctggagggg ttcgcgttgt aggtctcgac ggccttgttt       480
agatttgtaa cgtatgcttc gtgactgcga tggtttgatt tcaaccctgt tcttctttgg    540
tttctagtgc ctagctctct tactgtttgc tgtggtgcag ctccatgatc tgggctgaga    600
tgtgcggctc gagagcctgg aagaggggtc agcgggtgcg accgcgaaca caagtacggg    660
gat                                                                  663
```

<210> 13
<211> 703
<212> DNA
<213> *Pythium ultimum var. ultimum*

<400> 13
```
tcagaagaaa ggtttcctac ctcagacagc gtacgccatc ctttactttc atttcgcgct     60
gggggtttcca cacctaaca cttgcacaca tgttagactc cttggtccgt gtttcaagac    120
gggccgaatc gctccatttc gtcaaagtcc cgaacggcaa aagttactct agatctcaat    180
cgaccaatca ctccgtcagc atagcaagct atccaaacag gtaaccaaac gagagtccca    240
aacactttaa agcacattgt aggcacctca gtcccaacca cgacaactaa ctaccaagat    300
ataacagcca agagcaagct cctaacctac ctcctcagta gccatttctc acagcatacg    360
aactgactct gacgtcccac cgcaacacag ggcaccaaca agcaaacgca gaacagcaca    420
aagagcagaa aaccacttct tacatactgc acgcacctac tcgccaatga aatatgctac    480
agattataga cactggatac gattcgcttc cctttcagca gtttcaggta ctctttaact    540
ctcttttcaa agttctttc atctttccct cacggtactt gttcgctatc ggtctcgcac    600
caatatttag cttagatgg aatttaccac ctactttgcg ctgcagtccc aaacaacgcg    660
actcaaagaa aacgtgtcgt acgcacaagc tactcaggca caa                      703
```

<210> 14
<211> 18
<212> DNA
<213> Artificial Sequence

<220>
<223> Primer for fungal detection

<400> 14
```
gctcagcctt caacttgt                                                    18
```

<210> 15
<211> 45
<212> DNA
<213> Artificial Sequence

<220>
<223> Primer for fungal detection

<400> 15
```
gcctttccag aatccctttg cttttgaag gaaccctttc ccatc                       45
```

<210> 16
<211> 19
<212> DNA
<213> Artificial Sequence

<220>
<223> Primer for fungal detection

<400> 16
```
ggtggaattg acaagcgta                                                   19
```

SEQUENCE LISTING

```
<210> 17
<211> 43
<212> DNA
<213> Artificial Sequence

<220>
<223> Primer for fungal detection

<400> 17
atgctccgcg catgagagtt ttcttctcat cgagatcagt gtc          43

<210> 18
<211> 21
<212> DNA
<213> Artificial Sequence

<220>
<223> Primer for fungal detection

<400> 18
ccgttaatag gaagccaagg a                                  21

<210> 19
<211> 19
<212> DNA
<213> Artificial Sequence

<220>
<223> Primer for fungal detection

<400> 19
tccatcagca ccaagatcg                                     19

<210> 20
<211> 20
<212> DNA
<213> Artificial Sequence

<220>
<223> Primer for fungal detection

<400> 20
atttaccttg gccaacctتt                                    20

<210> 21
<211> 41
<212> DNA
<213> Artificial Sequence

<220>
<223> Primer for fungal detection

<400> 21
gcttcacacg ctgctccttt ttggagtcct cagcgataga t            41

<210> 22
<211> 19
<212> DNA
<213> Artificial Sequence

<220>
<223> Primer for fungal detection

<400> 22
tgtagctggc tccattagt                                     19

<210> 23
<211> 41
<212> DNA
<213> Artificial Sequence

<220>
<223> Primer for fungal detection

<400> 23
ggggtagggg tcccaatcat ttttgcacac cttttgctct t            41
```

SEQUENCE LISTING

```
<210> 24
<211> 22
<212> DNA
<213> Artificial Sequence

<220>
<223> Primer for fungal detection

<400> 24
tagctggatc tcagtgttat gc                                    22

<210> 25
<211> 19
<212> DNA
<213> Artificial Sequence

<220>
<223> Primer for fungal detection

<400> 25
ctcccatcca tgtctctgc                                        19

<210> 26
<211> 18
<212> DNA
<213> Artificial Sequence

<220>
<223> Primer for fungal detection

<400> 26
aatgtgtgaa gcccgaag                                         18

<210> 27
<211> 42
<212> DNA
<213> Artificial Sequence

<220>
<223> Primer for fungal detection

<400> 27
gcttccctga cggcttctct tttctcagag ttgccgttgt ag              42

<210> 28
<211> 22
<212> DNA
<213> Artificial Sequence

<220>
<223> Primer for fungal detection

<400> 28
gtcgcagagg aatctaacat aa                                    22

<210> 29
<211> 44
<212> DNA
<213> Artificial Sequence

<220>
<223> Primer for fungal detection

<400> 29
aggaactgcg agtcggttat tgtttttaca ggcagaccat ctcc            44

<210> 30
<211> 22
<212> DNA
<213> Artificial Sequence

<220>
<223> Primer for fungal detection

<400> 30
acagtactga cattctgcca at                                    22
```

SEQUENCE LISTING

```
<210> 31
<211> 19
<212> DNA
<213> Artificial Sequence

<220>
<223> Primer for fungal detection

<400> 31
acactccatc gctgtcaag                                                    19

<210> 32
<211> 20
<212> DNA
<213> Artificial Sequence

<220>
<223> Primer for fungal detection

<400> 32
tgaactccat ctcgtccata                                                   20

<210> 33
<211> 18
<212> DNA
<213> Artificial Sequence

<220>
<223> Primer for fungal detection

<400> 33
tcgtatgagc accaagga                                                     18

<210> 34
<211> 19
<212> DNA
<213> Artificial Sequence

<220>
<223> Primer for fungal detection

<400> 34
gatgttcaag cgtgtcagc                                                    19

<210> 35
<211> 19
<212> DNA
<213> Artificial Sequence

<220>
<223> Primer for fungal detection

<400> 35
gctggccttg atgttgttc                                                    19

<210> 36
<211> 42
<212> DNA
<213> Artificial Sequence

<220>
<223> Primer for fungal detection

<400> 36
cggtaactcg actgccatcc ttttccttac gacggaacat gg                          42

<210> 37
<211> 44
<212> DNA
<213> Artificial Sequence

<220>
<223> Primer for fungal detection

<400> 37
cccctttggtg ggatgtcaca attttctcgt cgtacttcgt tgag                       44
```

SEQUENCE LISTING

```
<210> 38
<211> 19
<212> DNA
<213> Artificial Sequence

<220>
<223> Primer for fungal detection

<400> 38
ttgaagtaga cgctcatgc                                              19

<210> 39
<211> 19
<212> DNA
<213> Artificial Sequence

<220>
<223> Primer for fungal detection

<400> 39
gtgctgcttt ctggtatga                                              19

<210> 40
<211> 18
<212> DNA
<213> Artificial Sequence

<220>
<223> Primer for fungal detection

<400> 40
cgttcaccgc tctgacat                                               18

<210> 41
<211> 19
<212> DNA
<213> Artificial Sequence

<220>
<223> Primer for fungal detection

<400> 41
cgctagaaat ggtctgcct                                              19

<210> 42
<211> 43
<212> DNA
<213> Artificial Sequence

<220>
<223> Primer for fungal detection

<400> 42
ttcgtcctgc ttgtggctct tttgccgttg tacctgtatc aat                   43

<210> 43
<211> 41
<212> DNA
<213> Artificial Sequence

<220>
<223> Primer for fungal detection

<400> 43
ttgctgtcga gaccgtgctt tttgacccgt actgacttct t                     41

<210> 44
<211> 18
<212> DNA
<213> Artificial Sequence

<220>
<223> Primer for fungal detection

<400> 44
ggtaaccaaa tcggtgct                                               18
```

SEQUENCE LISTING

```
<210> 45
<211> 19
<212> DNA
<213> Artificial Sequence

<220>
<223> Primer for fungal detection

<400> 45
gcgagtcggt tattgaact                                                  19

<210> 46
<211> 19
<212> DNA
<213> Artificial Sequence

<220>
<223> Primer for fungal detection

<400> 46
tttcgtcgca aaggtcact                                                  19

<210> 47
<211> 21
<212> DNA
<213> Artificial Sequence

<220>
<223> Primer for fungal detection

<400> 47
aacaagcaag gctaacactc t                                               21

<210> 48
<211> 41
<212> DNA
<213> Artificial Sequence

<220>
<223> Primer for fungal detection

<400> 48
gggtttgacc gccgagtttt ttgcgtacaa ctccgatact c                         41

<210> 49
<211> 43
<212> DNA
<213> Artificial Sequence

<220>
<223> Primer for fungal detection

<400> 49
ggaatctggc aaaagggtgg attttttgctc actggagatg gtt                      43

<210> 50
<211> 19
<212> DNA
<213> Artificial Sequence

<220>
<223> Primer for fungal detection

<400> 50
ttgaagtaga cgctcatgc                                                  19

<210> 51
<211> 18
<212> DNA
<213> Artificial Sequence

<220>
<223> Primer for fungal detection

<400> 51
gctgctttct ggtacgaa                                                   18
```

SEQUENCE LISTING

```
<210> 52
<211> 20
<212> DNA
<213> Artificial Sequence

<220>
<223> Primer for fungal detection

<400> 52
tcaccgctct gacatattgg                                                    20

<210> 53
<211> 18
<212> DNA
<213> Artificial Sequence

<220>
<223> Primer for fungal detection

<400> 53
gctggagatg gtttgcct                                                      18

<210> 54
<211> 42
<212> DNA
<213> Artificial Sequence

<220>
<223> Primer for fungal detection

<400> 54
ggagatcctc ggccacatgt tttcgaggta ccgttgtaac tg                           42

<210> 55
<211> 42
<212> DNA
<213> Artificial Sequence

<220>
<223> Primer for fungal detection

<400> 55
ttgctgtcga gaccgtgctt ttaccgtgat catccatcat tg                           42

<210> 56
<211> 19
<212> DNA
<213> Artificial Sequence

<220>
<223> Primer for fungal detection

<400> 56
gacgaagtac gacgagttc                                                     19

<210> 57
<211> 19
<212> DNA
<213> Artificial Sequence

<220>
<223> Primer for fungal detection

<400> 57
ctccacttct tcatggtcg                                                     19

<210> 58
<211> 19
<212> DNA
<213> Artificial Sequence

<220>
<223> Primer for fungal detection

<400> 58
cgatagccgt ggtaaggtc                                                     19
```

SEQUENCE LISTING

```
<210> 59
<211> 19
<212> DNA
<213> Artificial Sequence

<220>
<223> Primer for fungal detection

<400> 59
aggcagccat catgttctt                                                    19

<210> 60
<211> 44
<212> DNA
<213> Artificial Sequence

<220>
<223> Primer for fungal detection

<400> 60
gcccaaccta gaaggcacta acttttcct cgacctcctt catg                         44

<210> 61
<211> 41
<212> DNA
<213> Artificial Sequence

<220>
<223> Primer for fungal detection

<400> 61
ggtcaggtag cgaccgttgt tttgagttga cccagcagat g                           41

<210> 62
<211> 18
<212> DNA
<213> Artificial Sequence

<220>
<223> Primer for fungal detection

<400> 62
ttgtagggct caacaacc                                                     18

<210> 63
<211> 18
<212> DNA
<213> Artificial Sequence

<220>
<223> Primer for fungal detection

<400> 63
gacgcagttc tcgatgtc                                                     18

<210> 64
<211> 44
<212> DNA
<213> Artificial Sequence

<220>
<223> Primer for fungal detection

<400> 64
ggcacccttt tgatctccaa gattttggaa cgaccgagaa tgtg                        44

<210> 65
<211> 40
<212> DNA
<213> Artificial Sequence

<220>
<223> Primer for fungal detection

<400> 65
ataccggcac cggttccttt ttgatgcgag tgtcttcagg                             40
```

SEQUENCE LISTING

```
<210> 66
<211> 20
<212> DNA
<213> Artificial Sequence

<220>
<223> Primer for fungal detection

<400> 66
ccgtgaagaa taccccgatc                                              20

<210> 67
<211> 18
<212> DNA
<213> Artificial Sequence

<220>
<223> Primer for fungal detection

<400> 67
ccgagcgagt gggtaatc                                                18

<210> 68
<211> 22
<212> DNA
<213> Artificial Sequence

<220>
<223> Primer for fungal detection

<400> 68
aattagcaca acctggtaat ca                                           22

<210> 69
<211> 22
<212> DNA
<213> Artificial Sequence

<220>
<223> Primer for fungal detection

<400> 69
acttaatcca ggagctctca ta                                           22

<210> 70
<211> 48
<212> DNA
<213> Artificial Sequence

<220>
<223> Primer for fungal detection

<400> 70
gccatatctg gagcaccaat cattttaatg ttgttgtaac agcacatg               48

<210> 71
<211> 47
<212> DNA
<213> Artificial Sequence

<220>
<223> Primer for fungal detection

<400> 71
aatcaggtgc tggtacaggt tgttttaatc tactgaaggt cctgagt                47

<210> 72
<211> 22
<212> DNA
<213> Artificial Sequence

<220>
<223> Primer for fungal detection

<400> 72
aaccaccaat taatacaggc at                                           22
```

SEQUENCE LISTING

```
<210> 73
<211> 22
<212> DNA
<213> Artificial Sequence

<220>
<223> Primer for fungal detection

<400> 73
accattatca agtgtacaag ca                                        22

<210> 74
<211> 21
<212> DNA
<213> Artificial Sequence

<220>
<223> Primer for fungal detection

<400> 74
tgtacgatca ctgttagcat c                                         21

<210> 75
<211> 18
<212> DNA
<213> Artificial Sequence

<220>
<223> Primer for fungal detection

<400> 75
ctcgaccagt tcaagcag                                             18

<210> 76
<211> 41
<212> DNA
<213> Artificial Sequence

<220>
<223> Primer for fungal detection

<400> 76
ggcgtgccca tctttggtat tttgtgtcca cgaacctgaa g                   41

<210> 77
<211> 43
<212> DNA
<213> Artificial Sequence

<220>
<223> Primer for fungal detection

<400> 77
ggtgacaggg tcctggtctt tttgtggctt gttaaggatg aca                 43

<210> 78
<211> 18
<212> DNA
<213> Artificial Sequence

<220>
<223> Primer for fungal detection

<400> 78
ttgacatgtg ggagcacg                                             18

<210> 79
<211> 20
<212> DNA
<213> Artificial Sequence

<220>
<223> Primer for fungal detection

<400> 79
tcgtcgtgat aatgctgagg                                           20
```

SEQUENCE LISTING

<210> 80
<211> 19
<212> DNA
<213> Artificial Sequence

<220>
<223> Primer for fungal detection

<400> 80
cgttccagat gttctcgac                                                19

<210> 81
<211> 18
<212> DNA
<213> Artificial Sequence

<220>
<223> Primer for fungal detection

<400> 81
gtcaaggacg acgtaacg                                                 18

<210> 82
<211> 47
<212> DNA
<213> Artificial Sequence

<220>
<223> Primer for fungal detection

<400> 82
gcgtactacc tccaggttcg tattttgagc attgttagta ccttcca                 47

<210> 83
<211> 41
<212> DNA
<213> Artificial Sequence

<220>
<223> Primer for fungal detection

<400> 83
atgtccacgc cgaagatggt tttctgagca tcatcacgac g                       41

<210> 84
<211> 19
<212> DNA
<213> Artificial Sequence

<220>
<223> Primer for fungal detection

<400> 84
aacactgacg gatctgctt                                                19

<210> 85
<211> 18
<212> DNA
<213> Artificial Sequence

<220>
<223> Primer for fungal detection

<400> 85
tgacagggtc ctggtctt                                                 18

<210> 86
<211> 18
<212> DNA
<213> Artificial Sequence

<220>
<223> Primer for fungal detection

<400> 86
caaacgagag tcccaaac                                                 18

-continued

SEQUENCE LISTING

<210> 87
<211> 22
<212> DNA
<213> Artificial Sequence

<220>
<223> Primer for fungal detection

<400> 87
atccagtgtc tataatctgt ag                                    22

<210> 88
<211> 44
<212> DNA
<213> Artificial Sequence

<220>
<223> Primer for fungal detection

<400> 88
gagtcagttc gtatgctgtg agtttttaac agccaagagc aagc             44

<210> 89
<211> 44
<212> DNA
<213> Artificial Sequence

<220>
<223> Primer for fungal detection

<400> 89
cgcaacacag ggcaccaact tttgtgcagt atgtaagaag tggt             44

<210> 90
<211> 19
<212> DNA
<213> Artificial Sequence

<220>
<223> Primer for fungal detection

<400> 90
ggctactgag gaggtaggt                                         19

<210> 91
<211> 20
<212> DNA
<213> Artificial Sequence

<220>
<223> Primer for fungal detection

<400> 91
agaacagcac aaagagcaga                                        20

SEQUENCE LISTING

<160> NUMBER OF SEQ ID NOS: 91

<210> SEQ ID NO 1
<211> LENGTH: 912
<212> TYPE: DNA
<213> ORGANISM: Sclerotinia homoeocarpa

<400> SEQUENCE: 1
tagatctaca catggttctt acattatatt taggtcactt gatctacaag tgcggtggaa      60
ttgacaagcg tactattgaa aagttcgaga cggtatgact tctccacctt tctcttgcta     120
tcttttcccg tccttctcat cgagatcagt gtctgcgatc ttggtgctga tggatttatc    180

```
gggttgcgtt ttctctcatg cgcggagcat acatccgaat tctcaaccct ttgaacatta      240
ccacattgcc tttccagaat cccttttgcta acccgttaat aggaagccaa ggagatggga     300
aagggttcct tcaagtacgc atgggttttg acaagttga aggctgagcg tgagcgtggt      360
atcaccatcg acattgccct ctggaagttc gagacaccta agtacaatgt tactgtcatt     420
ggtatgtgta cgaattcttt atgccaactg aagtatatta acccattcgc agatgccccc    480
ggtcatcgtg atttcatcaa gaacatgatc actggtacct cccaagctga ttgtgccatt     540
cttatcatcg ctgccggtgt tggtgagttc gaggctggta tctccaagga tggtcagacc   600
cgtgagcacg ctcttcttgc gtacactctt ggtgttaagc aacttatcgt tgccatcaac     660
aagatggaca ccaccaagtg gtccaaggat cgtttcgagg aaatcatcaa ggagacaacc   720
aacttcatca agaaggttgg ctacaacgcc aagactgttc ccttcgtgcc gatctctgga     780
ttcgagggtg ataacatgat tgagccctca actaactgcc catggtacaa gggctgggag   840
agagagtcca aggagtctgg caaacacacc ggcaagaccc ttcttgaggc catcgacagc   900
atggacctgc ct                                                          912

<210> SEQ ID NO 2
<211> LENGTH: 629
<212> TYPE: DNA
<213> ORGANISM: Rhizoctonia solani AG2-2IIIB

<400> SEQUENCE: 2
tgtagctggc tccattagtt tggagcatgt gcacaccttt tgctcttttt ttaatccaca      60
cacacctgtg aacctgtgag gcagagacat ggatgggaga acttttattt actttaaaat    120
gaatgattgg gaccccctacc cccccccccc tctgtctact caactctaat ataaacccaa    180 tttatttttaa aatgaatgta atggatgtaa cgcatctaat actaagtttc aacaacggat     240
ctcttggctc tcgcatcgat gaagaacgca gcgaaatgcg ataagtaatg tgaattgcag    300
aattcagtga atcatcgaat ctttgaacgc accttgcgct ccttggtatt ccttggagca    360
tgcctgtttg agtatcatga atcttcaaa gtaaaccttt tgttaactc aatttggttt      420 cactttggta ttggaggttc ttgcagcttc acacgctgct cctctttgtt cattagctgg     480
atctcagtgt tatgcttggt tcctctcggc gtgataaatt atctatcgct gaggactccc    540
gataaaaagg ttggccaagg taaatgcaga tgaaccgctt ctaatagtcc attgacttgg    600
acaataaaat aattattatt ttacgatct                                        629

<210> SEQ ID NO 3
<211> LENGTH: 613
<212> TYPE: DNA
<213> ORGANISM: Microdochium nivale var. nivale

<400> SEQUENCE: 3
ggtaaccaaa tcggtgctgc tttctggtgc gtacacctcg actcgaagac gaccacgacc      60
ttcgcgacga aaatgaactc ggcagccaaa aaccgtgccg tcgagaatct ttagtcgcag    120
aggaatctaa cataagggtg gagaccggca aggctaacac tatcttccct gatacaggca    180
gaccatctcc ggcgagcacg gtcttgacag cgatggagtg taagttcaat aaccgactcg    240
cagttccttg cgagagaccg cttccctgac ggcttctcgg gccagatgaa atgcaacagt    300
actgacattc tgccaatagc tacaacggca actctgagct ccagctcgag cgcatgagcg    360
tctacttcaa cgaggtatgt caccatgggc gacttcgggc ttcacacatt cggccagcta    420
ctaactgacc acccacataa cttaggcttc cggcaacaag tacgttcccc gcgccgtcct    480
```

```
cgtcgatctc gagcccggta ccatggatgc cgtccgtgct ggtcccttcg gccagctgtt    540
ccgtcccgac aacttcgtct tcggtcagtc cggtgctggc aacaattggg ccaagggtca    600
ctacactgag ggt                                                       613
```

<210> SEQ ID NO 4
<211> LENGTH: 455
<212> TYPE: DNA
<213> ORGANISM: Pythium aphanidermatum

<400> SEQUENCE: 4

```
cttcagtgaa ctccatctcg tccatacccct caccagtgta ccagtgcaag aaggccttac     60
gacggaacat ggccgtgaac tgctcgctga cacgcttgaa catctcctgg atggcagtcg    120
agttaccgat gaacgtggcg ctcatcttga dacccctttgg tgggatgtca caaacgctgg    180
ccttgatgtt gttcgggatc cactcaacga agtacgacga gttcttgttc tgaacgttga    240
gcatctgctc gtcgacctcc ttggtgctca tacgaccacg aacatacaa gcggcggtca    300 ggtaacgacc gtgacgagga tcagcggcac acatcatgtt cttggcgtcg aactgctgct    360
gggtcagctc tggcaccgta agggcacggt actgctgcga gccgcgcgag gtgagcggag    420
cgaaaccgac catgaagaag tggaacgggg gaaaa                               455
```

<210> SEQ ID NO 5
<211> LENGTH: 518
<212> TYPE: DNA
<213> ORGANISM: Gaeumannomyces graminis var. avenae

<400> SEQUENCE: 5

```
ttagtgaccc ttggcccagt tgttgccagc accagactgg ccgaaaacga agttgtcggg     60
gcggaacagc tggccgaagg gaccggcacg aacggcgtcc atggtgccgg gctcgagatc    120
gacgaggacg gcacggggga catgcttgtt gccggaggcc tggagcggaa aggttatggg    180
tcagaataca tgatacgaag gtgggaaata ccggctgcta atgccggaca gaagcttcaa    240
ctcagggcct gtctgcatac ctcgttgaag tagacgctca tgcgctcgag ctggagctcc    300
gaggtgccgt tgtacctgta tcaatatgtc agagcggtga acggacggcg ggccgagcca    360
caagcaggac gaaatacgta cacgccattg ctgtcgagac cgtgctcgct agaaatggtc    420
tgcctgtcaa agaagtcagt acgggtcacg ggcagtggca gtcgtggtcg gcggcggatc    480
gtcgcgcggc gtcgtttcat accagaaagc agcaccgt                            518
```

<210> SEQ ID NO 6
<211> LENGTH: 550
<212> TYPE: DNA
<213> ORGANISM: Microdochium nivale var. majus

<400> SEQUENCE: 6

```
ggtaaccaaa tcggtgctgc tttctggtgc gtacaactcc gatactcaac gacggccgca     60
gtgacctttg cgacgaaaac aaactcggcg gtcaaacccg tatcgccgaa atcttcggt     120 cgcagaggaa tctggcaaaa gggtggaaat aaacaagcaa ggctaacact ctcttccccg    180
acacaggcaa accatctcca gtgagcacgg tctcgacagc aatggcgtgt aagttcaata    240
accgactcgc acttcttgcg aaaggccact tccctgatgg cgtatcacgc agatgaaat    300 acacaagtac tgcatcctg tcaatagcta caacggcacc tccgagctcc agctcgagcg    360
catgagtgtc tacttcaatg aggcttccgg caacaagtac gttcctcgtg ccgtccttgt    420
```

```
cgatctcgag cccggtacca tggatgccgt ccgtgctggt cccttcggcc agctgttccg    480
ccccgacaac ttcgtcttcg gtcagtccgg tgctggcaac aactgggcca agggtcacta    540
cactgagggt                                                           550
```

```
<210> SEQ ID NO 7
<211> LENGTH: 485
<212> TYPE: DNA
<213> ORGANISM: Magnaporthe poae

<400> SEQUENCE: 7
ttagtgaccc ttggcccagt tgttgccagc accggactgg ccgaaaacga agttgtcggg     60
gcggaacagc tggccgaagg gaccagcacg gacagcatcc atggtgccgg gctcgagatc    120
gaccaggacg gcacggggga catgcttgtt gccggaggcc tagagcgcgg ggaggcaatg    180
gtgtcagaaa acaacacgt ggttgcgaaa gagagacgcg ttcggagtct atctgcatac    240
ctcgttgaag tagacgctca tgcgctcgag ctggagctcc gaggtaccgt tgtaactgca    300
ccaatatgtc agagcggtga acggacatgt ggccgaggat ctcccaaaca gaatacatac    360
actccattgc tgtcgagacc gtgctcgctg gagatggttt gcctgcccag gaagtcagta    420
tcaatgatga tgatcacgg tcgtggtggg tgcgagcggt ggttcgtacc agaaagcagc    480
accgt                                                                485
```

```
<210> SEQ ID NO 8
<211> LENGTH: 539
<212> TYPE: DNA
<213> ORGANISM: Gaeumannomyces graminis var. avenae

<400> SEQUENCE: 8
cctcagtgaa ctccatctcg tccataccct cgccagtgta ccaatgaagg aaagccttgc     60
gcctgaacat ggcagtgaac tgctcaccaa cacgcttgaa gagctcttgt atggcagtcg    120
agtttccgat gaaggtcgac gacatcttca ggccccgggg agggattgag cagagggcgg    180
tctggatgtt gttgggaatc cactcgacga agtacgacga gttcttgttc tggatgttgc    240
gcatctggtc ctcgacctcc ttcatggaga ccttaccacg gctatcgcac acagggatgg    300
ttagttagtg ccttctaggt tgggcatatt aaatgggcca gataaataag cccaatgcct    360
agatgcaaga ctcacaaaat agcagagcag gtcaggtagc gaccgttgcg gaagtccgag    420
gcagccatca tgttcttggg gtcgaacatc tgctgggtca actcgggcac cgtgacggcg    480
cggaatgagt gggcgccgcg gctagtcagg ggagcgaagc cgaccatgaa gaagtggag    539
```

```
<210> SEQ ID NO 9
<211> LENGTH: 236
<212> TYPE: DNA
<213> ORGANISM: Rhizoctonia solani AG2-2IV

<400> SEQUENCE: 9
gttgtagggc tcaacaaccg tgtcggagac cttgggggaa ggaacgaccg agaatgtgca     60
catcatacga tcggggtatt cttcacggat cttggagatc aaaagggtgc ccataccggc    120
accggttcct ccaccgagcg agtgggtaat ctggaagccc tgaagacact cgcatccctc    180
ggcctctttg cgcgcgacat cgagaactgc gtcaacaagc tcggcacctt cggtgt       236
```

```
<210> SEQ ID NO 10
<211> LENGTH: 604
<212> TYPE: DNA
<213> ORGANISM: Pythium aphanidermatum
```

<400> SEQUENCE: 10

```
tgcttttca ggtgtagttg gtacaacttt atctgtttta attagaatgg aattagcaca      60
acctggtaat caaatttta tgggaaatca tcaattatat aatgttgttg taacagcaca    120
tgcttttata atgattttct tcatggttat gcctgtatta attggtggtt ttggtaactg    180
gtttattcct ttaatgattg gtgctccaga tatggctttt cctagaatga ataatattag    240
tttttggtta ttacctcctt cattattatt attagtatca tctgctatag tagaatcagg    300
tgctggtaca ggttggactg tatatccacc attatcaagt gtacaagcac actcaggacc    360
ttcagtagat ttagctattt ttagtttaca tttatctggt atttcttcat tattaggtgc    420
tattaatttt ttatcaacta tttataatat gagagctcct ggattaagtt ttcatagatt    480
gccattattt gttggtctg tttttattac agctttttta ttattgttaa cattaccagt    540
attagcaggt gctattacaa tgttattaac agatagaaat ttaaatactt cttttttatga    600
tcct                                                                 604
```

<210> SEQ ID NO 11
<211> LENGTH: 657
<212> TYPE: DNA
<213> ORGANISM: Colletotrichum graminicola

<400> SEQUENCE: 11

```
aatattctcg acatatgcag cctttccgtt gagatactat gtacgatcac tgttagcatc     60
tcttttcaaa aaaggtcttg ttggtgtcca cgaacctgaa ggtagtacgc gtgctcccac    120
atgtcaatac caaagatggg cacgcccttg gtgacagggt cctggtcttt cgtcgtgata    180
atgctgaggc ccgttatgtc atccttaaca agccacccc agccgctacc ggtgataccc    240
agcagcgtgg tgttgaaagc ctgcttgaac tggtcgagcc cgcccagac gcgggtgatc    300
tcggcgacga gctttggcgc cgcatcgggc gaggcatcac cgctcgaggc tggggaaagg    360
ttctcccaga atagggaatg gttgatgtgg ccgccgccgt tgaagtttag ggccgcgagg    420
acggcgatgc gattctggag cgggtttgca ttgtaagtct cgatggcctt gttcagattt    480
gtaacgtatg cttgatggct gtaggtggct tcatgtcaac tctcttcttc gctgcttcat    540
atttcatggt tatctcactg tttgctgtgg tgcagctcca tgatctgagc tgagatgtga    600
ggctcgaggg cctgcaggag gggtcagcgg gcgcgatcgc gagcacgagt aagggat      657
```

<210> SEQ ID NO 12
<211> LENGTH: 663
<212> TYPE: DNA
<213> ORGANISM: Colletotrichum cereale

<400> SEQUENCE: 12

```
cgttccagat gttctcgacg tacgccgctt ttccattgag gtactgaggc cgagcattgt     60
tagtaccttc caacaaagca gatccgtcag tgtttacgaa cctggaggta gtacgcgtgc    120
tcccacatgt ccacgccgaa gatgggcacg cccttggtga cagggtcctg gtctttcgtc    180
gtgatgatgc tcagacccgt tacgtcgtcc ttgaccagcc atcccagcc gctgccggtg    240
atacccagaa gcgtggcgtt gaaagcctgc ttgaactggt cgagcccgcc ccagacccgg    300
gcgatctcag cgacgagctt cggcgcggcg tctggcgagg cgtctgggct cgaggcaggg    360
gacaggtttt cccagaagag gggagtggtt gatgtggccg ccgccgttga gttgagggct    420
gggaggacgg cgatgcggtt ctggaggggg ttcgcgttgt aggtctcgac ggccttgttt    480
```

```
agatttgtaa cgtatgcttc gtgactgcga tggtttgatt tcaaccctgt tcttctttgg    540
tttctagtgc ctagctctct tactgtttgc tgtggtgcag ctccatgatc tgggctgaga    600
tgtgcggctc gagagcctgg aagaggggtc agcgggtgcg accgcgaaca caagtacggg    660
gat                                                                  663
```

<210> SEQ ID NO 13
<211> LENGTH: 703
<212> TYPE: DNA
<213> ORGANISM: Pythium ultimum var. ultimum

<400> SEQUENCE: 13

```
tcagaagaaa ggtttcctac ctcagacagc gtacgccatc ctttactttc atttcgcgct     60 ggggttttcca caccctaaca cttgcacaca tgttagactc cttggtccgt gtttcaagac   120
gggccgaatc gctccatttc gtcaaagtcc cgaacggcaa aagttactct agatctcaat   180
cgaccaatca ctccgtcagc atagcaagct atccaaacag gtaaccaaac gagagtccca   240
aacactttaa agcacattgt aggcacctca gtcccaacca cgacaactaa ctaccaagat   300
ataacagcca agagcaagct cctaacctac ctcctcagta gccatttctc acagcatacg   360
aactgactct gacgtcccac cgcaacacag ggcaccaaca agcaaacgca gaacagcaca   420
aagagcagaa aaccacttct tacatactgc acgcacctac tcgccaatga aatatgctac   480
agattataga cactggatac gattcgcttc cctttcagca gtttcaggta ctctttaact   540
ctcttttcaa agttctttc atcttttccct cacggtactt gttcgctatc ggtctcgcac   600
caatatttag ctttagatgg aatttaccac ctactttgcg ctgcagtccc aaacaacgcg   660
actcaaagaa aacgtgtcgt acgcacaagc tactcaggca caa                      703
```

<210> SEQ ID NO 14
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 14

```
gctcagcctt caacttgt                                                   18
```

<210> SEQ ID NO 15
<211> LENGTH: 45
<212> TYPE: DNA
<213> ORGANISM: Artificial Sequence
<220> FEATURE:
<223> OTHER INFORMATION: Primer for fungal detection

<400> SEQUENCE: 15

```
gcctttccag aatccctttg cttttgaag gaacccttc ccatc                       45
```

<210> SEQ ID NO 16
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 16

```
ggtggaattg acaagcgta                                                  19
```

<210> SEQ ID NO 17
<211> LENGTH: 43

```
<212> TYPE: DNA
<213> ORGANISM: Artificial Sequence
<220> FEATURE:
<223> OTHER INFORMATION: Primer for fungal detection

<400> SEQUENCE: 17
atgctccgcg catgagagtt ttcttctcat cgagatcagt gtc                43

<210> SEQ ID NO 18
<211> LENGTH: 21
<212> TYPE: DNA
<213> ORGANISM: Artificial Sequence
<220> FEATURE:
<223> OTHER INFORMATION: Primer for fungal detection

<400> SEQUENCE: 18
ccgttaatag gaagccaagg a                                         21

<210> SEQ ID NO 19
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 19
tccatcagca ccaagatcg                                            19

<210> SEQ ID NO 20
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 20
atttaccttg gccaaccttt                                           20

<210> SEQ ID NO 21
<211> LENGTH: 41
<212> TYPE: DNA
<213> ORGANISM: Artificial Sequence
<220> FEATURE:
<223> OTHER INFORMATION: Primer for fungal detection

<400> SEQUENCE: 21
gcttcacacg ctgctccttt ttggagtcct cagcgataga t                   41

<210> SEQ ID NO 22
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 22
tgtagctggc tccattagt                                            19

<210> SEQ ID NO 23
<211> LENGTH: 41
<212> TYPE: DNA
<213> ORGANISM: Artificial Sequence
<220> FEATURE:
<223> OTHER INFORMATION: Primer for fungal detection
```

-continued

```
<400> SEQUENCE: 23
ggggtagggg tcccaatcat ttttgcacac cttttgctct t                41

<210> SEQ ID NO 24
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 24
tagctggatc tcagtgttat gc                                    22

<210> SEQ ID NO 25
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 25
ctcccatcca tgtctctgc                                        19

<210> SEQ ID NO 26
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 26
aatgtgtgaa gcccgaag                                         18

<210> SEQ ID NO 27
<211> LENGTH: 42
<212> TYPE: DNA
<213> ORGANISM: Artificial Sequence
<220> FEATURE:
<223> OTHER INFORMATION: Primer for fungal detection

<400> SEQUENCE: 27
gcttccctga cggcttctct tttctcagag ttgccgttgt ag              42

<210> SEQ ID NO 28
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 28
gtcgcagagg aatctaacat aa                                    22

<210> SEQ ID NO 29
<211> LENGTH: 44
<212> TYPE: DNA
<213> ORGANISM: Artificial Sequence
<220> FEATURE:
<223> OTHER INFORMATION: Primer for fungal detection

<400> SEQUENCE: 29
aggaactgcg agtcggttat tgtttttaca ggcagaccat ctcc            44

<210> SEQ ID NO 30
```

```
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 30
acagtactga cattctgcca at                                            22

<210> SEQ ID NO 31
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 31
acactccatc gctgtcaag                                                19

<210> SEQ ID NO 32
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 32
tgaactccat ctcgtccata                                               20

<210> SEQ ID NO 33
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 33
tcgtatgagc accaagga                                                 18

<210> SEQ ID NO 34
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 34
gatgttcaag cgtgtcagc                                                19

<210> SEQ ID NO 35
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 35
gctggccttg atgttgttc                                                19

<210> SEQ ID NO 36
<211> LENGTH: 42
<212> TYPE: DNA
<213> ORGANISM: Artificial Sequence
<220> FEATURE:
<223> OTHER INFORMATION: Primer for fungal detection
```

```
<400> SEQUENCE: 36
cggtaactcg actgccatcc ttttccttac gacggaacat gg                          42

<210> SEQ ID NO 37
<211> LENGTH: 44
<212> TYPE: DNA
<213> ORGANISM: Artificial Sequence
<220> FEATURE:
<223> OTHER INFORMATION: Primer for fungal detection

<400> SEQUENCE: 37
ccctttggtg ggatgtcaca attttctcgt cgtacttcgt tgag                        44

<210> SEQ ID NO 38
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 38
ttgaagtaga cgctcatgc                                                    19

<210> SEQ ID NO 39
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 39
gtgctgcttt ctggtatga                                                    19

<210> SEQ ID NO 40
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 40
cgttcaccgc tctgacat                                                     18

<210> SEQ ID NO 41
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 41
cgctagaaat ggtctgcct                                                    19

<210> SEQ ID NO 42
<211> LENGTH: 43
<212> TYPE: DNA
<213> ORGANISM: Artificial Sequence
<220> FEATURE:
<223> OTHER INFORMATION: Primer for fungal detection

<400> SEQUENCE: 42
ttcgtcctgc ttgtggctct tttgccgttg tacctgtatc aat                         43

<210> SEQ ID NO 43
```

<211> LENGTH: 41
<212> TYPE: DNA
<213> ORGANISM: Artificial Sequence
<220> FEATURE:
<223> OTHER INFORMATION: Primer for fungal detection

<400> SEQUENCE: 43
ttgctgtcga gaccgtgctt tttgacccgt actgacttct t         41

<210> SEQ ID NO 44
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 44
ggtaaccaaa tcggtgct                                    18

<210> SEQ ID NO 45
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 45
gcgagtcggt tattgaact                                   19

<210> SEQ ID NO 46
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 46
tttcgtcgca aaggtcact                                   19

<210> SEQ ID NO 47
<211> LENGTH: 21
<212> TYPE: DNA
<213> ORGANISM: Artificial Sequence
<220> FEATURE:
<223> OTHER INFORMATION: Primer for fungal detection

<400> SEQUENCE: 47
aacaagcaag gctaacactc t                                21

<210> SEQ ID NO 48
<211> LENGTH: 41
<212> TYPE: DNA
<213> ORGANISM: Artificial Sequence
<220> FEATURE:
<223> OTHER INFORMATION: Primer for fungal detection

<400> SEQUENCE: 48
gggtttgacc gccgagtttt ttgcgtacaa ctccgatact c          41

<210> SEQ ID NO 49
<211> LENGTH: 43
<212> TYPE: DNA
<213> ORGANISM: Artificial Sequence
<220> FEATURE:
<223> OTHER INFORMATION: Primer for fungal detection

```
<400> SEQUENCE: 49
ggaatctggc aaaagggtgg atttttgctc actggagatg gtt         43

<210> SEQ ID NO 50
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 50
ttgaagtaga cgctcatgc                                    19

<210> SEQ ID NO 51
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 51
gctgctttct ggtacgaa                                     18

<210> SEQ ID NO 52
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 52
tcaccgctct gacatattgg                                   20

<210> SEQ ID NO 53
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 53
gctggagatg gtttgcct                                     18

<210> SEQ ID NO 54
<211> LENGTH: 42
<212> TYPE: DNA
<213> ORGANISM: Artificial Sequence
<220> FEATURE:
<223> OTHER INFORMATION: Primer for fungal detection

<400> SEQUENCE: 54
ggagatcctc ggccacatgt tttcgaggta ccgttgtaac tg          42

<210> SEQ ID NO 55
<211> LENGTH: 42
<212> TYPE: DNA
<213> ORGANISM: Artificial Sequence
<220> FEATURE:
<223> OTHER INFORMATION: Primer for fungal detection

<400> SEQUENCE: 55
ttgctgtcga gaccgtgctt ttaccgtgat catccatcat tg          42

<210> SEQ ID NO 56
```

<211> LENGTH: 19
<212> TYPE: DNA
<213> ORGANISM: Artificial Sequence
<220> FEATURE:
<223> OTHER INFORMATION: Primer for fungal detection

<400> SEQUENCE: 56
gacgaagtac gacgagttc                                              19

<210> SEQ ID NO 57
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 57
ctccacttct tcatggtcg                                              19

<210> SEQ ID NO 58
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 58
cgatagccgt ggtaaggtc                                              19

<210> SEQ ID NO 59
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 59
aggcagccat catgttctt                                              19

<210> SEQ ID NO 60
<211> LENGTH: 44
<212> TYPE: DNA
<213> ORGANISM: Artificial Sequence
<220> FEATURE:
<223> OTHER INFORMATION: Primer for fungal detection

<400> SEQUENCE: 60
gcccaaccta gaaggcacta acttttcct cgacctcctt catg                   44

<210> SEQ ID NO 61
<211> LENGTH: 41
<212> TYPE: DNA
<213> ORGANISM: Artificial Sequence
<220> FEATURE:
<223> OTHER INFORMATION: Primer for fungal detection

<400> SEQUENCE: 61
ggtcaggtag cgaccgttgt tttgagttga cccagcagat g                     41

<210> SEQ ID NO 62
<211> LENGTH: 18
<212> TYPE: DNA
<213> ORGANISM: Artificial Sequence
<220> FEATURE:
<223> OTHER INFORMATION: Primer for fungal detection

```
<400> SEQUENCE: 62
ttgtagggct caacaacc                                                   18

<210> SEQ ID NO 63
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 63
gacgcagttc tcgatgtc                                                   18

<210> SEQ ID NO 64
<211> LENGTH: 44
<212> TYPE: DNA
<213> ORGANISM: Artificial Sequence
<220> FEATURE:
<223> OTHER INFORMATION: Primer for fungal detection

<400> SEQUENCE: 64
ggcacccttt tgatctccaa gattttggaa cgaccgagaa tgtg                      44

<210> SEQ ID NO 65
<211> LENGTH: 40
<212> TYPE: DNA
<213> ORGANISM: Artificial Sequence
<220> FEATURE:
<223> OTHER INFORMATION: Primer for fungal detection

<400> SEQUENCE: 65
ataccggcac cggttccttt ttgatgcgag tgtcttcagg                           40

<210> SEQ ID NO 66
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 66
ccgtgaagaa taccccgatc                                                 20

<210> SEQ ID NO 67
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 67
ccgagcgagt gggtaatc                                                   18

<210> SEQ ID NO 68
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 68
aattagcaca acctggtaat ca                                              22

<210> SEQ ID NO 69
```

```
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 69
acttaatcca ggagctctca ta                                              22

<210> SEQ ID NO 70
<211> LENGTH: 48
<212> TYPE: DNA
<213> ORGANISM: Artificial Sequence
<220> FEATURE:
<223> OTHER INFORMATION: Primer for fungal detection

<400> SEQUENCE: 70
gccatatctg gagcaccaat cattttaatg ttgttgtaac agcacatg                  48

<210> SEQ ID NO 71
<211> LENGTH: 47
<212> TYPE: DNA
<213> ORGANISM: Artificial Sequence
<220> FEATURE:
<223> OTHER INFORMATION: Primer for fungal detection

<400> SEQUENCE: 71
aatcaggtgc tggtacaggt tgttttaatc tactgaaggt cctgagt                   47

<210> SEQ ID NO 72
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 72
aaccaccaat taatacaggc at                                              22

<210> SEQ ID NO 73
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 73
accattatca agtgtacaag ca                                              22

<210> SEQ ID NO 74
<211> LENGTH: 21
<212> TYPE: DNA
<213> ORGANISM: Artificial Sequence
<220> FEATURE:
<223> OTHER INFORMATION: Primer for fungal detection

<400> SEQUENCE: 74
tgtacgatca ctgttagcat c                                               21

<210> SEQ ID NO 75
<211> LENGTH: 18
<212> TYPE: DNA
<213> ORGANISM: Artificial Sequence
<220> FEATURE:
<223> OTHER INFORMATION: Primer for fungal detection
```

<400> SEQUENCE: 75
ctcgaccagt tcaagcag                                          18

<210> SEQ ID NO 76
<211> LENGTH: 41
<212> TYPE: DNA
<213> ORGANISM: Artificial Sequence
<220> FEATURE:
<223> OTHER INFORMATION: Primer for fungal detection

<400> SEQUENCE: 76
ggcgtgccca tctttggtat tttgtgtcca cgaacctgaa g                41

<210> SEQ ID NO 77
<211> LENGTH: 43
<212> TYPE: DNA
<213> ORGANISM: Artificial Sequence
<220> FEATURE:
<223> OTHER INFORMATION: Primer for fungal detection

<400> SEQUENCE: 77
ggtgacaggg tcctggtctt tttgtggctt gttaaggatg aca              43

<210> SEQ ID NO 78
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 78
ttgacatgtg ggagcacg                                          18

<210> SEQ ID NO 79
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 79
tcgtcgtgat aatgctgagg                                        20

<210> SEQ ID NO 80
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 80
cgttccagat gttctcgac                                         19

<210> SEQ ID NO 81
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 81
gtcaaggacg acgtaacg                                          18

<210> SEQ ID NO 82

```
<211> LENGTH: 47
<212> TYPE: DNA
<213> ORGANISM: Artificial Sequence
<220> FEATURE:
<223> OTHER INFORMATION: Primer for fungal detection

<400> SEQUENCE: 82
gcgtactacc tccaggttcg tattttgagc attgttagta ccttcca                47

<210> SEQ ID NO 83
<211> LENGTH: 41
<212> TYPE: DNA
<213> ORGANISM: Artificial Sequence
<220> FEATURE:
<223> OTHER INFORMATION: Primer for fungal detection

<400> SEQUENCE: 83
atgtccacgc cgaagatggt tttctgagca tcatcacgac g                      41

<210> SEQ ID NO 84
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 84
aacactgacg gatctgctt                                               19

<210> SEQ ID NO 85
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 85
tgacagggtc ctggtctt                                                18

<210> SEQ ID NO 86
<211> LENGTH: 18
<212> TYPE: DNA
<213> ORGANISM: Artificial Sequence
<220> FEATURE:
<223> OTHER INFORMATION: Primer for fungal detection

<400> SEQUENCE: 86
caaacgagag tcccaaac                                                18

<210> SEQ ID NO 87
<211> LENGTH: 22
<212> TYPE: DNA
<213> ORGANISM: Artificial Sequence
<220> FEATURE:
<223> OTHER INFORMATION: Primer for fungal detection

<400> SEQUENCE: 87
atccagtgtc tataatctgt ag                                           22

<210> SEQ ID NO 88
<211> LENGTH: 44
<212> TYPE: DNA
<213> ORGANISM: Artificial Sequence
<220> FEATURE:
<223> OTHER INFORMATION: Primer for fungal detection
```

```
<400> SEQUENCE: 88
gagtcagttc gtatgctgtg agtttttaac agccaagagc aagc                    44

<210> SEQ ID NO 89
<211> LENGTH: 44
<212> TYPE: DNA
<213> ORGANISM: Artificial Sequence
<220> FEATURE:
<223> OTHER INFORMATION: Primer for fungal detection

<400> SEQUENCE: 89
cgcaacacag ggcaccaact tttgtgcagt atgtaagaag tggt                    44

<210> SEQ ID NO 90
<211> LENGTH: 19
<212> TYPE: DNA
<213> ORGANISM: Artificial Sequence
<220> FEATURE:
<223> OTHER INFORMATION: Primer for fungal detection

<400> SEQUENCE: 90
ggctactgag gaggtaggt                                                19

<210> SEQ ID NO 91
<211> LENGTH: 20
<212> TYPE: DNA
<213> ORGANISM: Artificial Sequence
<220> FEATURE:
<223> OTHER INFORMATION: Primer for fungal detection

<400> SEQUENCE: 91
agaacagcac aaagagcaga                                               20
```

What is claimed is:

1. A method for detecting *Sclerotinia* homoeocarpa DNA in a turf grass sample with a loop-mediated isothermal amplification (LAMP) assay, comprising:
   subjecting the turf sample to a LAMP reaction
   with a primer set having sequences which are at least 90% identical to SEQ ID NOs:14, 15, 16, and 17.

2. The method according to claim 1, wherein the primer set further comprises sequences which are at least 90% identical to SEQ ID NOs: 18 and 19.

3. A kit for the detection of fungal DNA in a turf grass sample using a LAMP assay, comprising one or more than one of the primer sets identified in claim 1.

4. The method according to claim 1, wherein the primer set comprises primers identical to SEQ ID NOs:14, 15, 16, and 17.

5. The method according to claim 1, wherein the primer set comprises primers identical to SEQ ID NOs:14, 15, 16, 17, 18, and 19.

6. The method according to claim 1, wherein the primer set consists of primers 90% identical to SEQ ID NOs:14, 15, 16, 17, 18, and 19.

7. The method according to claim 1, wherein the primer set consists of primers identical to SEQ ID NOs:14, 15, 16, 17, 18, and 19.

* * * * *